US011709169B2

(12) United States Patent
Leung et al.

(10) Patent No.: US 11,709,169 B2
(45) Date of Patent: Jul. 25, 2023

(54) LIPID ABNORMALITIES AND ASSOCIATION WITH ATOPIC ALLERGIC DISEASES

(71) Applicant: National Jewish Health, Denver, CO (US)

(72) Inventors: Donald Y. M. Leung, Denver, CO (US); Elena Goleva, Denver, CO (US); Evgeny Berdyshev, Littleton, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 15/890,881

(22) Filed: Feb. 7, 2018

(65) Prior Publication Data

US 2018/0224470 A1 Aug. 9, 2018

Related U.S. Application Data

(60) Provisional application No. 62/455,791, filed on Feb. 7, 2017.

(51) Int. Cl.
*G01N 33/92* (2006.01)
*C12Q 1/6883* (2018.01)

(52) U.S. Cl.
CPC ........... *G01N 33/92* (2013.01); *C12Q 1/6883* (2013.01); *C12Q 2600/158* (2013.01); *G01N 2405/04* (2013.01); *G01N 2405/08* (2013.01); *G01N 2800/202* (2013.01); *G01N 2800/24* (2013.01)

(58) Field of Classification Search
CPC ............... G01N 33/92; G01N 2800/22; G01N 2405/08; G01N 2800/24; G01N 2405/04; G01N 2800/202; C12Q 1/6883; C12Q 2600/158
See application file for complete search history.

(56) References Cited

U.S. PATENT DOCUMENTS

| | | | | |
|---|---|---|---|---|
| 2006/0024268 A1* | 2/2006 | Kasaian | G01N 33/6869 | 424/85.2 |
| 2010/0120042 A1* | 5/2010 | Noh | C12Q 1/6886 | 435/6.18 |
| 2012/0208193 A1* | 8/2012 | Okino | C12Q 1/6806 | 435/6.11 |

FOREIGN PATENT DOCUMENTS

| | | | |
|---|---|---|---|
| WO | WO-2014015439 A1 * | 1/2014 | G01N 33/6881 |
| WO | WO-2015095451 A * | 6/2015 | A61P 35/04 |
| WO | WO-2016164795 A1 * | 10/2016 | A61K 31/164 |

OTHER PUBLICATIONS

Belgrave, DCM et al. Curr Derm Rep. 2015. 4: 221-227. (Year: 2015).*
Thomsen, SF. ISRN Allergy. 2014. 2014: Article ID 354250. 7 pages. (Year: 2014).*
Jensen, J et al. Journal of Investigative Dermatology. 2004. 122(6): 1423-1431. (Year: 2004).*
Shimizu, Y et al. Journal of Dermatological Science. 2014. 74: 162-165. (Year: 2014).*
Park, YH et al. Journal of Investigative Dermatology. 2012. 132: 476-479. (Year: 2012).*
Ewald, DA et al. BMC Medical Genomics. 2015. 8: 60. 15 pages. (Year: 2015).*
Lampe, MA et al. Human stratum corneum lipids: characterization and regional variations. Journal of Lipid Research. 1983. 24: 120-130. (Year: 1983).*
Tawada, C et al. Interferon-gamma decreases ceramides with long-chain fatty acids: Possible involvement in atopic dermatitis and psoriasis. Journal of Investigative Dermatology. 2014. 134: 712-718. (Year: 2014).*
Van Smeden, J et al. Stratum corneum lipids: Their role for the skin barrier function in healthy subjects and atopic dermatitis patients. In: Agner, T [editor]. Current Problems in Dermatology (Basel). 2016. pp. 8-26. Skin Barrier Function. (Year: 2016).*
Levin, J et al. Atopic dermatitis and the stratum corneum, Part 2: Other structural and functional characteristics of the stratum corneum barrier in atopic skin. J. Clin. Aesthet. Dermatol. 2013. 6(11): 49-54. (Year: 2013).*
Skolova, B et al. Different phase behavior and packing of ceramides with long (C16) and very long (C24) acyls in model membranes: Infrared spectroscopy using deuterated lipids. The Journal of Physical Chemistry B. 2014. 118: 10460-10470. (Year: 2014).*
Park, Y-H et al. Decrease of ceramides with very long-chain fatty acids and downregulation of elongases in a murine atopic dermatitis model. Journal of Investigative Dermatology. 2012. 132: 476-479. (Year: 2012).*
Hara, J et al. High-expression of sphingomyelin deacylase is an important determinant of ceramide deficiency leading to barrier disruption in atopic dermatitis. The Journal of Investigative Dermatology. 2000. 115(3): 406-413. (Year: 2000).*
Bieber et al. "Clinical phenotypes and endophenotypes of atopic dermatitis: Where are we, and where should we go?" J Allergy Clin Immunol, Apr. 2017, vol. 139, No. 4, pp. S58-S64.
Broccardo et al. "Peeling off the layers: skin taping and a novel proteomics approach to study atopic dermatitis," J Allergy Clin Immunol, Nov. 2009, vol. 124, Nov. 5, pp. 1113-1115 e1-11.
Brunner et al. "The immunology of atopic dermatitis and its reversibility with broad-spectrum and targeted therapies," J Allergy Clin Immunol, Apr. 2017, vol. 139, No. 4, pp. E65-E76.
Eichenfield et al. "Current guidelines for the evaluation and management of atopic dermatitis: A comparison of the Joint Task Force Practice Parameter and American Academy of Dermatology guidelines," J Allergy Clin Immunol, Apr. 2017, vol. 139, No. 4, pp. E49-E57.
Elias et al. "Mechanisms of abnormal lamellar body secretion and the dysfunctional skin barrier in atopic dermatitis," J Allergy Clin Immunol., Oct. 2014, vol. 134, No. 4, pp. 781-791.

(Continued)

*Primary Examiner* — Renee Claytor
*Assistant Examiner* — Susan E. Fernandez
(74) *Attorney, Agent, or Firm* — Sheridan Ross P.C.

(57) ABSTRACT

The present invention is related to novel methods for identifying a population of subjects that are at risk for developing of atopic allergic diseases, such as atopic dermatitis, and to the prevention and treatment of these allergic diseases.

6 Claims, 13 Drawing Sheets

(56) References Cited

OTHER PUBLICATIONS

Elias "Lipid abnormalities and lipid-based repair strategies in atopic dermatitis," Biochim Biophys Acta, Mar. 2014, vol. 1841, No. 3, pp. 323-330.
Ishikawa et al. "Changes in the Ceramide Profile of Atopic Dermatitis Patients," Journal of Investigative Dermatology, 2010, vol. 130, No. 10, pp. 2511-2514.
Janssens et al. "Increase in short-chain ceramides correlates with an altered lipid organization and decreased barrier function in atopic eczema patients," Journal of Lipid Research, 2012, vol. 53, No. 12, pp. 2755-2766.
Kihara "Synthesis and degradation pathways, functions, and pathology of ceramides and epidermal acylceramides," Progress in Lipid Research, 2016, vol. 63, pp. 50-69.
Leung et al. "Deciphering the complexities of atopic dermatitis: Shifting paradigms in treatment approaches," J Allergy Clin Immunol, Oct. 2014, vol. 134, No. 4, pp. 769-779.
Li et al. "Altered composition of epidermal lipids correlates with *Staphylococcus aureus* colonization status in atopic dermatitis," British Journal of Dermatology, 2017, vol. 177, pp. e125-e127.
Li et al. "Lipidomic analysis of epidermal lipids: a tool to predict progression of inflammatory skin disease in humans," Expert Rev Proteomics, May 2016, vol. 13, No. 5, pp. 451-456.
Sahle et al. "Skin Diseases Associated with the Depletion of Stratum Corneum Lipids and Stratum Corneum Lipid Substitution Therapy," Skin Pharmacology and Physiology, 2015, vol. 28, No. 1, pp. 42-55.
Van Smeden et al. "The importance of free fatty acid chain length for the skin barrier function in atopic eczema patients," Experimental Dermatology, 2014, vol. 23, No. 1, pp. 45-52.

* cited by examiner

NS-Ceramides (S-C18)
% NS-Ceramides (S-C18)
NC
AD Non-Lesional
AD Lesional
14:0-CER
16:0-CER
18:1-CER
18:0-CER
20:0-CER
22:1-CER
22:0-CER
24:1-CER
24:0-CER
26:1-CER
26:0-CER
28:1-CER
28:0-CER
30:1-CER
30:0-CER
32:1-CER
32:0-CER Sphingomyelins
% Total Sphingomyelins
16:0-SM
18:0-SM
20:0-SM
22:0-SM
24:1-SM
24:0-SM
26:1-SM
26:0-SM
28:0-SM Lyso-PCs
% Total LPC
14:0-LPC
16:0-LPC
18:0-LPC
18:1-LPC
18:2-LPC
18:3-LPC
20:0-LPC
20:1-LPC
20:2-LPC
20:4-LPC
20:5-LPC
22:0-LPC
22:1-LPC
22:4-LPC
22:5-LPC
22:6-LPC
24:0-LPC
26:0-LPC
28:0-LPC
30:0-LPC NS-NDS-CER C20-NS-CER C20-AS-CER AS-CER
C22-NS-CER C22-AS-CER NP-CER AP-CER
LPC SM-DHSM EOS-CER 3 days of $Ca^{2+}$ differentiation

5 days of $Ca^{2+}$ differentiation p<0.01
IL-13, normalized counts
2000
1500
1000
500
10
8
6
4
2
0
NC
AD NL
AD Lesional p<0.05
p<0.001
IL-4R, normalized counts
1000
800
600
400
200
0
NC
AD NL
AD Lesional Fig. 10A
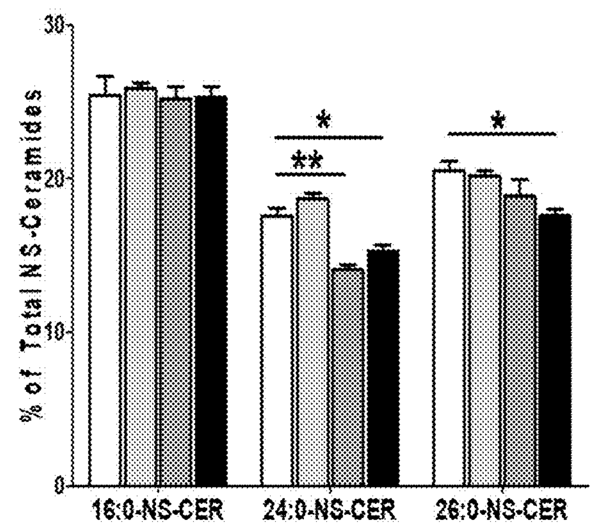
Fig. 10B
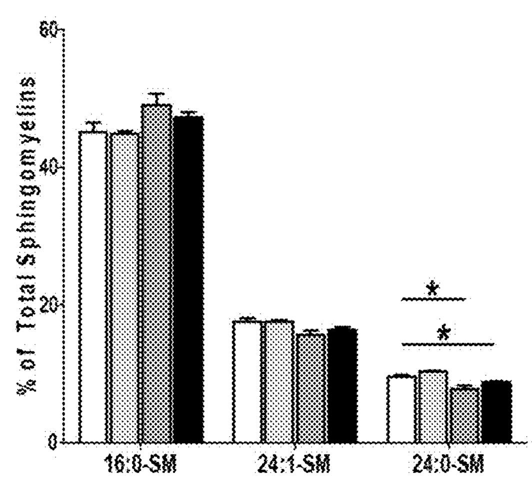
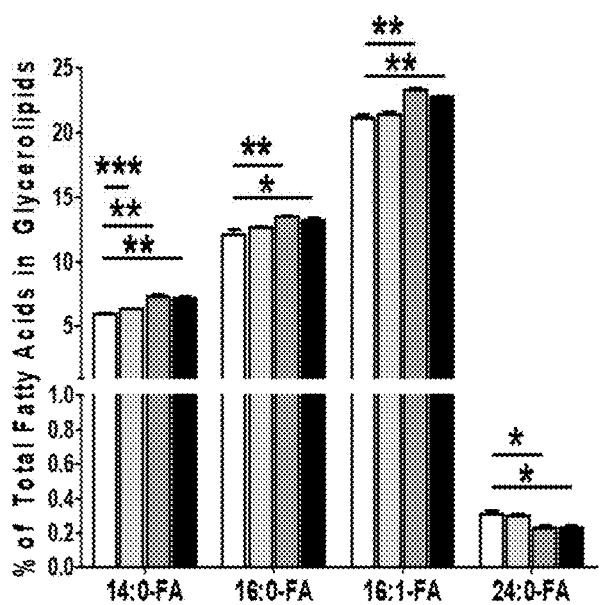
Fig. 10C
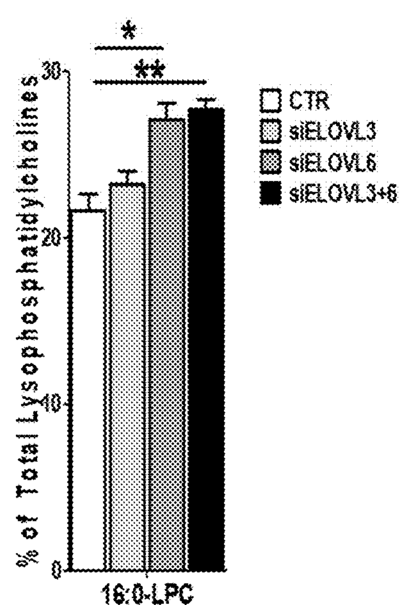
Fig. 10D

LIPID ABNORMALITIES AND ASSOCIATION WITH ATOPIC ALLERGIC DISEASES

CROSS-REFERENCE TO RELATED APPLICATIONS

This application claims the benefit of priority under 35 U.S.C. § 119(e) to U.S. Provisional Patent Application No. 62/455,791, filed Feb. 7, 2017. The entire disclosure of U.S. Provisional Patent Application No. 62/455,791 is incorporated herein by reference.

GOVERNMENT RIGHTS

This invention was made with government support under grant number 1 U19 AI117673 awarded by the National Institutes of Health/National Institute of Allergy and Infectious Diseases (NIH/NIAID). The government has certain rights in the invention.

FIELD OF THE INVENTION

The present invention is directed toward the diagnosing and identifying of a population of subjects that are at risk for developing an allergic disease, such as atopic dermatitis (AD) and food allergy, and to the prevention and treatment of an allergic disease in such subjects.

BACKGROUND OF THE INVENTION

Per the World Allergy Organization, the natural history of atopic manifestations is referred to as "Allergic March" or "Atopic March" and is characterized by a typical sequence of allergic responses and clinical symptoms which may appear early in life, persist over years or decades and often do not remit spontaneously with age. The allergic diseases that often begin early in life include AD, food allergy, asthma and allergic rhinitis. In general, no clinical symptoms except a dry skin are detectable at birth. Immunoglobulin E (IgE) responses directed to food proteins may be observed during the first weeks or months of life. In all parts of the world they are commonly directed to proteins from hen's egg, nuts and cow's milk, independent of the mode of feeding (breastfeeding versus formula feeding). These strong infantile IgE antibody responses to food proteins can be considered as markers for atopic reactivity in general, since they have been demonstrated to be predictors of subsequent sensitization to other food proteins (peanuts, tree nuts) or aeroallergens from the indoor or outdoor environment. Sensitization to environmental allergens requires more time and is generally observed during the pre-school or early school-age period. In many atopic individuals, AD is the first clinical manifestation with the highest incidence during the first months of life, and the highest period prevalence during the first three years of life (worldallergy.org). Over 50% of patients with AD develop respiratory allergies including asthma and allergic rhinitis.

AD is a chronic inflammatory skin disorder that affects nearly 17% of children and can persist into adulthood. Advances in understanding the mechanisms underlying AD require direct sampling of AD skin. Although AD is primarily a skin disease involving infants and young children, there are few skin-based studies examining AD in this age group because of the invasiveness of skin biopsies. AD is often associated with food allergy and asthma. The abnormal skin barrier in patients with AD allow epicutaneous absorption of environmental food and airborne allergens through the skin and promote systemic allergen sensitization, which predisposes to the development of food allergy and respiratory allergy (Broccardo C J, et al. Peeling off the layers: skin taping and a novel proteomics approach to study atopic dermatitis. J Allergy Clin Immunol 2009; 124:1113-5 e1-11; Leung D Y, Guttman-Yassky E. Deciphering the complexities of atopic dermatitis: shifting paradigms in treatment approaches. J Allergy Clin Immunol 2014; 134:769-79). AD is a complex disease with a genetic predisposition strongly influenced by innate and adaptive immune responses, as well as environmental factors, including allergen exposure, irritants', microbes, diet, stress, and air quality (Leung D Y, Guttman-Yassky E. Deciphering the complexities of atopic dermatitis: shifting paradigms in treatment approaches. J Allergy Clin Immunol 2014; 134:769-79).

AD is a serious systemic disease with lesional skin manifestations that severely impact the quality of life of affected patients (Bieber T., et al. Clinical phenotypes and endophenotypes of atopic dermatitis: Where are we, and where should we go? *J Allergy Clin Immunol.* 2017; 139 (4S):S58-S64; Brunner P M., et al. The immunology of atopic dermatitis and its reversibility with broad-spectrum and targeted therapies. *J Allergy Clin Immunol.* 2017; 139 (4S):S65-S76; Eichenfield L F., et al. Current guidelines for the evaluation and management of atopic dermatitis: A comparison of the Joint Task Force Practice Parameter and American Academy of Dermatology guidelines. *J Allergy Clin Immunol.* 2017; 139(4S): S49-S57). AD has been linked to dysregulated and overactivated type 2 immune response in the skin with a special role for IL-4/IL-13-driven signaling in AD pathogenesis (Brunner P M, et al. 2017; Leung D Y, and Guttman-Yassky E. Deciphering the complexities of atopic dermatitis: shifting paradigms in treatment approaches. *J Allergy Clin Immunol.* 2014; 134(4): 769-79). This type 2 hyperactivation blocks terminal differentiation of skin keratinocytes and formation of a mature stratum corneum. An intact skin barrier is required to protect the human body from water loss and to prevent the penetration of allergens and pathogens into the skin and underlying tissues. Lipids play an important role in the formation of a fully functional stratum corneum. In a healthy human epidermis, lipids are primarily composed of ceramides, sterols, and free fatty acids with minimal presence of other lipids that usually represent the majority of lipids in any other tissue and in the circulation (Kihara A. Synthesis and degradation pathways, functions, and pathology of ceramides and epidermal acylceramides. *Prog Lipid Res.* 2016; 63(50-69)). In comparison to other skin lipids, ceramides receive special attention as their content and unique composition is thought to largely determine the efficiency of protective barrier properties of the skin. In particular, human skin ceramides contain an unusually high proportion of very long chain fatty acids and have substantial quantities of unique highly hydrophobic omega-esterified (EOS) ceramides. It has been reported that there is a decrease in the chain length of ceramide-associated fatty acids in the lesional and non-lesional skin of AD patients (Janssens M, et al. Increase in short-chain ceramides correlates with an altered lipid organization and decreased barrier function in atopic eczema patients. *J Lipid Res.* 2012; 53(12):2755-66; Ishikawa J, et al. Changes in the ceramide profile of atopic dermatitis patients. *J Invest Dermatol.* 2010; 130(10):2511-4; van Smeden J, et al. The importance of free fatty acid chain length for the skin barrier function in atopic eczema patients. *Exp Dermatol.* 2014; 23(1):45-52; Li S, et al. Altered composition of epidermal lipids correlates with *Staphylococcus aureus* colonization status in atopic dermatitis. *Br J Dermatol*. 2017). However, only minimal information is available about other lipids that can be associated with AD development. Currently, there is no understanding of what leads to lipid changes during AD pathogenesis and how one could affect AD severity or even prevent its development by targeting lipid metabolic processes to preserve or restore normal skin lipid composition. In addition, as current treatment approaches are not curative, there is considerable interest in studying approaches to prevent AD as well as other allergic diseases, including use of strategies to improve skin barrier or downregulate the type 2 allergic immune response. This is hindered by the lack of biomarkers to identify AD prior to its occurrence (Kim J, et al; Epidermal thymic stromal lymphopoietin predicts the development of atopic dermatitis during infancy. J. Allergy Clin Immunol 2016; 137(4):1282-5; Leung D Y, Guttman-Yassky E. Deciphering the complexities of atopic dermatitis: shifting paradigms in treatment approaches. J Allergy Clin Immunol 2014; 134:769-79).

SUMMARY OF INVENTION

One embodiment of the invention relates to a method to identify a subject at risk of developing an allergic disease comprising obtaining at least one skin sample from the subject; determining the level and relative percentage of short chain molecular species and long chain molecular species of at least one lipid in the skin sample; comparing the level and/or relative percentage of the short chain molecular species of the at least one lipid in the skin sample to the same short chain molecular species of lipid from a healthy control sample; comparing the level and/or relative percentage of the long chain molecular species of the at least one lipid in the skin sample to the same long chain molecular species of lipid from a healthy control sample; and identifying the subject as at risk of developing an allergic disease when: (i) the level and/or relative percentage of short chain molecular species from the skin sample is elevated as compared to the level and/or relative percentage of the same short chain molecular species from the healthy control sample; and (ii) the level and/or relative percentage of long chain molecular species from the skin sample is decreased as compared to the level and/or relative percentage of the same long chain molecular species from the healthy control sample.

Another embodiment of the inventions relates to a method of diagnosing and treating an allergic disease in an symptomatic subject comprising obtaining at least one skin sample from the subject; determining the level and relative percentage of short chain molecular species and long chain molecular species of at least one lipid in the skin sample; comparing the level and relative percentage of the short chain molecular species of the at least one lipid in the skin sample to the same short chain molecular species of lipid from a healthy control sample; comparing the level and relative percentage of the long chain molecular species of the at least one lipid in the skin sample to the same long chain molecular species of lipid from a healthy control sample; identifying the subject as having an allergic disease when: (i) the level and/or relative percentage of short chain molecular species from the skin sample is elevated as compared to the level and/or relative percentage of the same short chain molecular species from the healthy control sample; and (ii) the level and/or relative percentage of long chain molecular species from the skin sample is decreased as compared to the level and/or relative percentage of the same long chain molecular species from the healthy control sample; and administering an effective amount of a therapeutic to the subject prior to development of allergic disease symptoms.

In one aspect of the method of diagnosing and treating an allergic disease in an asymptomatic subject, the therapeutic is selected from the group consisting of a moisturizer, an anti-inflammatory, modifier of an enzyme of lipid metabolism, a long chain fatty acid derivative and combinations thereof.

In one aspect of the method of diagnosing and treating an allergic disease in an asymptomatic subject further comprises administration of a different therapeutic as compared to the therapeutic administered previously.

In one aspect of the method of diagnosing and treating an allergic disease in an asymptomatic subject, administration of the therapeutic delays the onset of symptoms of the allergic disease in the subject.

In one aspect of the method of diagnosing and treating an allergic disease in an asymptomatic subject, administration of the therapeutic reduces the severity of the allergic disease symptoms in the subject.

In any of the embodiments of the invention described above or elsewhere herein, the allergic disease is selected from the group consisting of AD, eczema, food allergy, asthma, allergic rhinitis and combinations thereof.

In any of the embodiments of the inventions described above or elsewhere in herein, the skin sample is obtained by a skin tape stripping method.

In any of the embodiments of the invention described above or elsewhere wherein, the step of determining the level and/or relative percentage of the at least one lipid is by a method comprising mass-spectrometry.

In any of the embodiments of the inventions described above or elsewhere in herein, the short chain molecular species of at least one lipid is a selected from the group consisting of short chain NS-ceramides, short chain sphingomyelins, short chain lysophosphatidylcholines, and combinations thereof.

In any of the embodiments of the inventions described above or elsewhere in herein, the long chain molecular species of at least one lipid is a selected from the group consisting of long chain NS-ceramides, long chain sphingomyelins, long chain lysophosphatidylcholines, and combinations thereof.

In any of the embodiments of the inventions described above or elsewhere in herein, the method(s) further comprises determining the expression level of one or more lipid metabolism enzymes in the at least one skin sample. In one aspect, the one or more lipid metabolism enzymes is selected from the group consisting of elongation of long chain fatty acids family member 1 (ELOVL1), elongation of long chain fatty acids family member 1 (ELOVL1), elongation of long chain fatty acids family member 2 (ELOVL2), elongation of long chain fatty acids family member 3 (ELOVL3), elongation of long chain fatty acids family member 4 (ELOVL4), elongation of long chain fatty acids family member 5 (ELOVL5), elongation of long chain fatty acids family member 6 (ELOVL6), elongation of long chain fatty acids family member 7 (ELOVL7), and combinations thereof. In yet another aspect, the expression levels of ELOVL3 and ELOVL6 from the skin sample is decreased as compared to the expression levels of ELOVL3 and ELOVL6 from the healthy control sample.

BRIEF DESCRIPTION OF THE DRAWINGS

FIG. 6A show the effect of $Ca^{2+}$-induced differentiation in vitro on relative proportion of selected ceramides in keratinocytes. Each ceramide molecular specie was quantified by targeted LC-ESI-MS/MS, normalized by sample total lipid phosphorus content, and data were expressed as relative percentage within each lipid subclass. Each individual data point was expressed relative to an average of non-differentiated control. Note the decrease in relative content of short-chain ceramides and the increase in long-chain ceramides. STAT6 controls IL-4/IL-13 effect on ceramides (FIG. 6B), sphingomyelins (FIG. 6C) in differentiated keratinocytes. No differences in LPC are observed in the keratinocyte model (FIG. 6D). Keratinocytes were differentiated in the absence or presence of IL-4/IL-13. Keratinocytes were treated with STAT6 siRNA during five-day differentiation period. Lipids were quantified by LC-ESI-MS/MS and normalized by total lipid phosphorus content. n=3.

FIGS. 10A-10D show the silencing of ELOVL3 and ELOVL6 results in changes in long-chain and short-chain species within several classes of lipids in $Ca^{2+}$-differentiated human keratinocytes in vitro. Relative proportion of selected species of NS-ceramides (FIG. 10A), sphingomyelins (FIG. 10B), fatty acids in global glycerolipids (FIG. 10C), and palmitoylglycerolphosphocholine (16:0-LPC) (FIG. 10D) within corresponding classes of lipids is presented. Note that silencing of ELOVL3 and especially ELOVL6 results in the decrease in relative proportion of long chain species in sphingomyelins, NS-ceramides, and lignoceric acids (24:0-FA) while increasing the proportion of short-chain LPC (16:0-LPC) and globally within fatty acids in glycerolipids.

DETAILED DESCRIPTION OF THE INVENTION

Figures 1A, 1B, 1C:
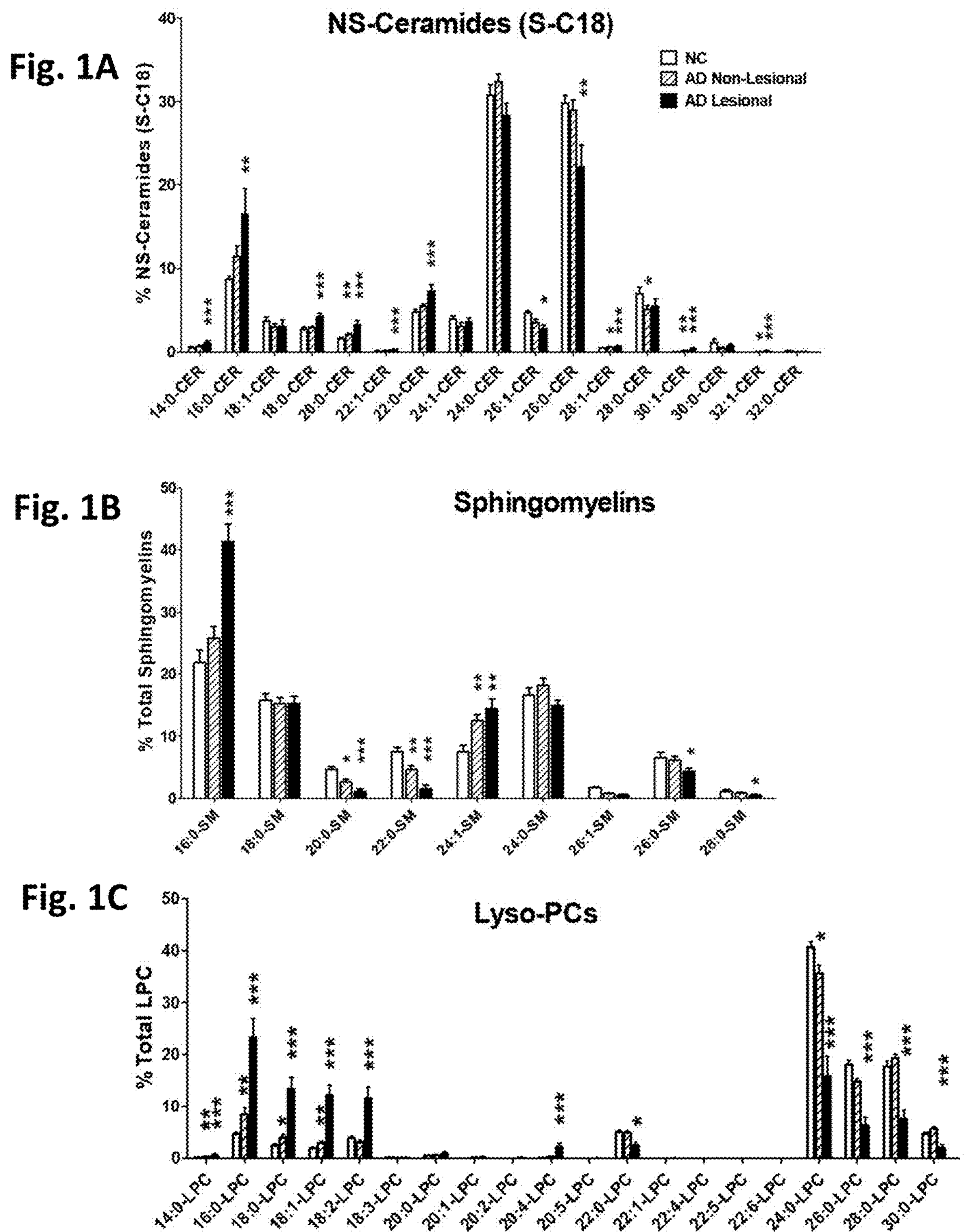
FIGS. 1A-1C show the changes in relative level of short- and long-chain molecular species in ceramides (FIG. 1A), sphingomyelins (FIG. 1B), and lysophosphatidylcholines (FIG. 1C) in stratum corneum of AD patients as compared to skin of normal healthy control subjects (NC). Each lipid molecular specie was quantified by targeted liquid chromatography-electrospray ionization-tandem mass spectrometry (LC-ESI-MS/MS), normalized by sample total protein content, and data were expressed as relative percentage within each lipid subclass. *p<0.05, p<0.01, *p<0.001 as compared to NC. AD lesional skin—n=15, AD non-lesional skin—n=30, NC skin—n=25.

The present invention generally relates to novel methods for predicting and/or identifying subjects predisposed to developing an allergic disease, as well as, to methods to diagnose, treat and prevent an allergic disease. These allergic diseases can include allergic diseases that often begin early in life (referred to herein as “infantile allergic diseases”) and include diseases and/or conditions associated with a defective skin barrier such as AD, as well as food allergies, asthma and allergic rhinitis.

The inventors have found that for prevention and/or treatment of allergic diseases such as AD, it is important to identify subjects, such as human infants, predisposed or at risk to the development of allergic diseases as well as subjects having AD with and without one or more food allergies. The inventors have made the novel finding that there are novel lipid changes in the nonlesional skin of subjects with allergic disease such as AD, and that these changes can precede the development of allergic diseases including AD. The novel lipid changes identified by the inventors can account for reduced skin barrier function including increased transdermal water loss in AD skin and its predisposition for bacterial colonization.

Lipids in the stratum corneum of AD patients differ substantially in composition from healthy subjects. As disclosed herein, the inventors have analyzed the stratum corneum lipids from non-lesional and lesional skin of AD subjects and interleukin-13 (IL-13) skin-specific transgenic mice. The inventors also directly examined the effects of IL-4/IL-13 on human keratinocytes in vitro. As provided in the Examples herein, mass spectrometric analysis of lesional stratum corneum from AD subjects and IL-13 transgenic mice revealed an increased proportion of short-chain (N-14:0-24:0) non-hydroxy fatty acid sphingosine ceramides (NS-ceramides), sphingomyelins, and 14:0-22:0-lysophosphatidylcholines (LPCs) with a simultaneous decline in the proportion of corresponding long-chain species (N-26:0-32:0 sphingolipids and 24:0-30:0-LPC) when compared to healthy controls. An increase in short-chain LPC species was also observed in non-lesional AD skin. Similar changes were observed in IL-4/IL-13-driven responses in $Ca^{2+}$-differentiated human keratinocytes in vitro, all being blocked by signal transducer and activator for transcription 6 (STAT6) silencing with siRNA. RNA sequencing analysis performed on stratum corneum of AD as compared to healthy subjects identified decreased expression of fatty acid elongases: elongation of long chain fatty acids family member 3 (ELOVL3) and elongation of long chain fatty acid family member 6 (ELOVL6) that contributed to observed changes in atopic skin lipids. Inhibition of ELOVL3 and ELOVL6 expression was observed in IL-4/IL-13 treated keratinocyte cultures. STAT6 siRNA reversed inhibitory effects of these cytokines on ELOVL3 and ELOVL6 expression in keratinocytes. Thus, the novel findings by the inventors show a pathogenic role of type 2 immune activation in AD skin lipid metabolism.

The critical importance of type 2 immune pathway activation in the pathogenesis of AD has recently been demonstrated by the significant clinical improvement of moderate to severe AD following treatment with biologics that interfere with IL-4/IL-13 action, such as antibodies directed to the alpha subunit of the interleukin-4 receptor (DUPILUMABD®) (Simpson E L, et al. Two Phase 3 Trials of Dupilumab versus Placebo in Atopic Dermatitis. *N Engl J Med.* 2016; 375(24):2335-48). The loss of skin barrier function is the hallmark of AD, and lipids play a fundamental role in forming the proper hydrophobic barrier in stratum corneum that reduces transepidermal water loss. In AD skin, however, this lipid derived barrier is not properly formed, and very little is known about what drives the lipid changes in AD skin (Elias P M. Lipid abnormalities and lipid-based repair strategies in atopic dermatitis. *Biochim Biophys Acta.* 2014; 1841(3):323-30).

Skin lipids are unique in many aspects and provide a pivotal role to form a proper skin barrier. Healthy epidermis has lipids that are mostly composed of ceramides, free fatty acids, and cholesterol (Feingold K R, et al. 2014; Li S, et al. Lipidomic analysis of epidermal lipids: a tool to predict progression of inflammatory skin disease in humans. *Expert Rev Proteomics.* 2016; 13(5):451-6) with very little presence of other lipids. Ceramides in the skin are particularly complex and are represented by at least twelve groups based on sphingoid base and type of fatty acid attached to it (Table 1). Skin ceramides are classified based on their sphingoid bases (LCBs) and fatty acids (FAs) that N-acylate sphingoid base. Sphingoid bases can be sphingosine (S), dihydrosphingosine (DS), phytosphingosine (P), and 6-hydroxy-sphingosine (H). Fatty acids can be non-hydroxy (N) and alfa-hydroxy (A). A separate class of omega-esterified (EO) ceramides provides the final four groups of ceramide subclasses based on sphingoid base in their structure (EOS, EODS, EOP, EOH). Current classification can be further extended based of the chain length of sphingoid base (in human skin, sphingoid bases with 18, 20, and 22 carbons are common). See Table 1.

TABLE 1

| Ceramides in the Skin | | | |
|---|---|---|---|
| | FAs | | |
| LCBs | Non-hydroxy FA (N) | α-hydroxy FA (A) | Esterified ω-hydroxy FA (EO) |
| Dihydro-Sph (DS) | NDS | ADS | EODS |
| Sph (S) | NS | AS | EOS |
| Phyto-Sph (P) | NP | AP | EOP |
| 6-OH-Sph (H) | NH | AH | EOH |

A very specific highly hydrophobic group of ceramides, so called ω-esterified (EOS) ceramides, is present only in the skin. Fatty acids are also unique in skin ceramides as they are unusually very long (up to 38 carbons (C38)) and hydrophobic, this also contributes to the overall requirement for highly rigid and hydrophobic structure to provide efficient barrier. Lesional, and in some cases non-lesional skin of AD patients has decreased proportion of EOS ceramides and other ceramides with very long chain fatty acids (Janssens, M, et al. 2012; Ishikawa J, et al. 2010; van Smeden J, et al. 2014; Li S, et al. 2017). Such change in skin lipid composition results in aberrant lipid organization in the lipid layers and positively correlates with the degree of transepidermal water loss in AD skin (Elias P M, and Wakefield J S. Mechanisms of abnormal lamellar body secretion and the dysfunctional skin barrier in patients with atopic dermatitis. *J Allergy Clin Immunol.* 2014; 134(4):781-91 e1; Sahle F F, et al. Skin diseases associated with the depletion of stratum corneum lipids and stratum corneum lipid substitution therapy. *Skin Pharmacol Physiol.* 2015; 28(1): 42-55).

Genetic abnormalities in the expression of filaggrin protein result in the aberrant lipid delivery into the lamellar bodies (Elias P M, et al. 2014; Gruber R, et al. Filaggrin genotype in ichthyosis vulgaris predicts abnormalities in epidermal structure and function. *Am J Pathol.* 2011; 178 (5):2252-63). It is not clear which exact mechanism would define such an effect—the abnormal transport of complex lipids into lamellar bodies or abnormal activity of enzymes responsible for their degradation into ceramides. However, filaggrin mutations cannot account for lipid abnormalities in all AD patients, as only a minority of caucasian AD patients have FLG mutations (Irvine A D, et al. Filaggrin mutations associated with skin and allergic diseases. *N Engl J Med.* 2011; 365(14):1315-27). At the same time, the inventors have demonstrated that type 2 cytokines can also significantly inhibit filaggrin expression in keratinocytes (Howell M D, et al. 2007), and such reduced levels of filaggrin can also affect lipid assembly in lamellar bodies. In addition, changes in stratum corneum lipid properties has been shown to correlate with disease severity but are independent of filaggrin mutations (Janssens M, et al. 2012). Cole et al. performed RNAseq analysis of non-lesional skin samples from AD patients and healthy controls and stratified the analysis of changes in AD transcriptome based on FLG gene mutations. The results found that patients with no FLG mutations had significant changes in the expression of enzymes involved in the metabolism and synthesis of lipids (Cole C, et al. Filaggrin-stratified transcriptomic analysis of pediatric skin identifies mechanistic pathways in patients with atopic dermatitis. *J Allergy Clin Immunol.* 2014; 134 (1):82-91). However, no information is currently available on signaling mechanisms and metabolic pathways that promote these changes in skin ceramides.

Figure 3A:
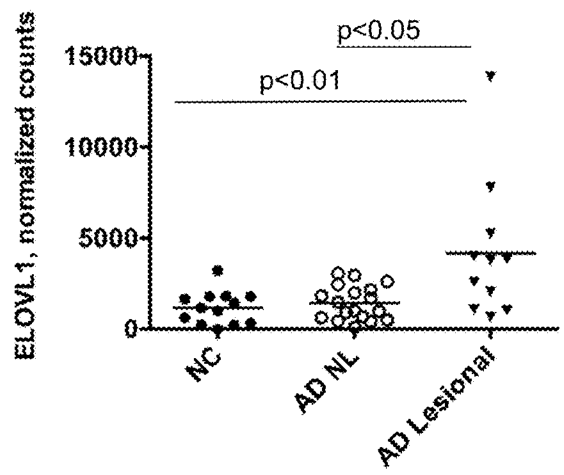
FIGS. 3A-3G show the expression pattern for ELOVL1-7 in human stratum corneum as detected by RNAseq analysis of skin tape strip RNA samples collected from AD patients and NC. The expression of ELOVL3 and ELOVL6 is decreased in lesional AD skin (both elongases take part in the formation of long-chain fatty acids). AD lesional skin—n=12, AD non-lesional skin—n=18, NC skin—n=13.
Figure 3B:
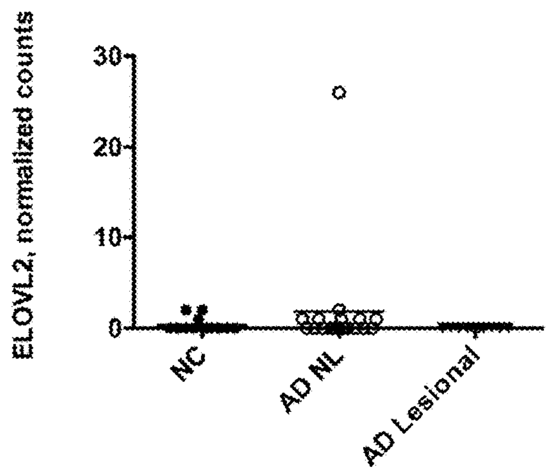
Figure 3C:
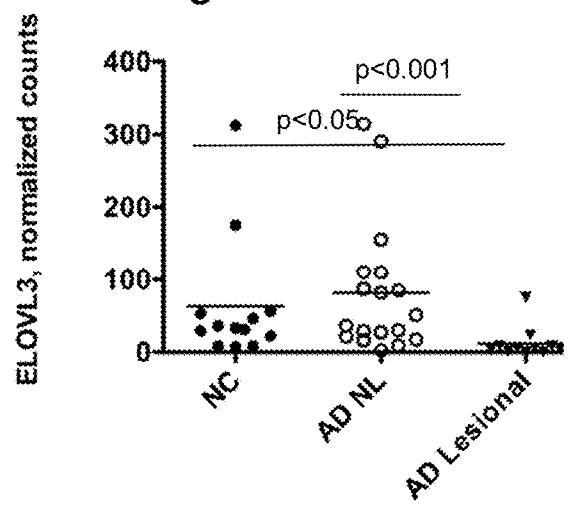
Figure 3D:
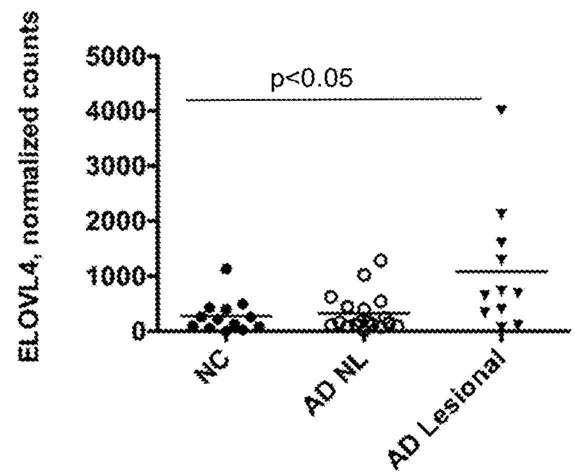
Figure 3E:
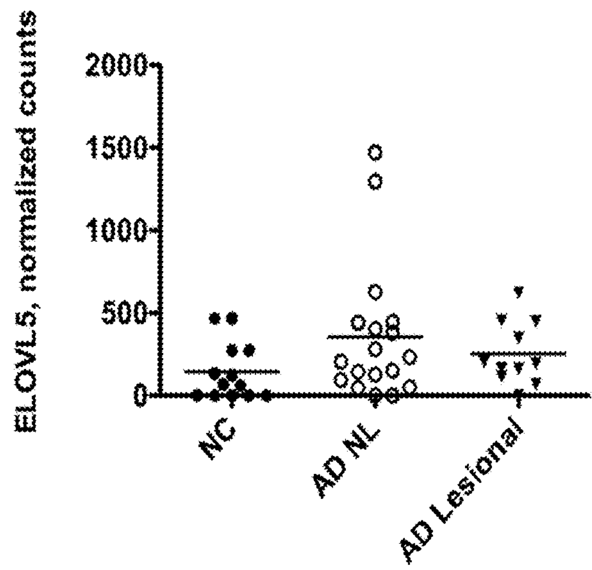
Figure 3F:
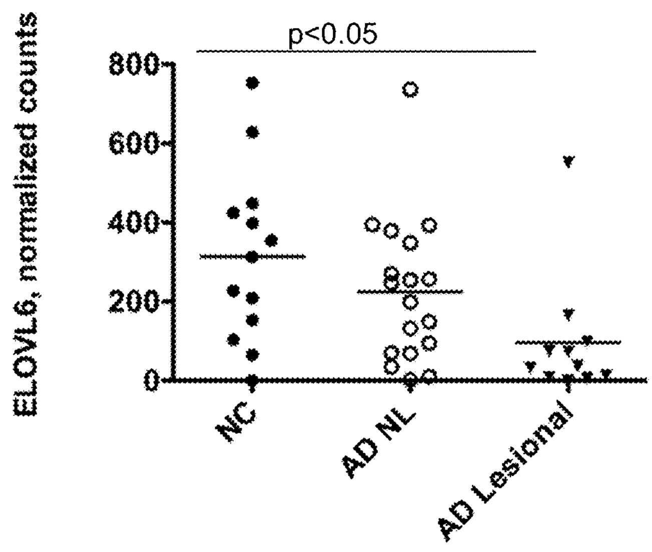
Figure 3G:
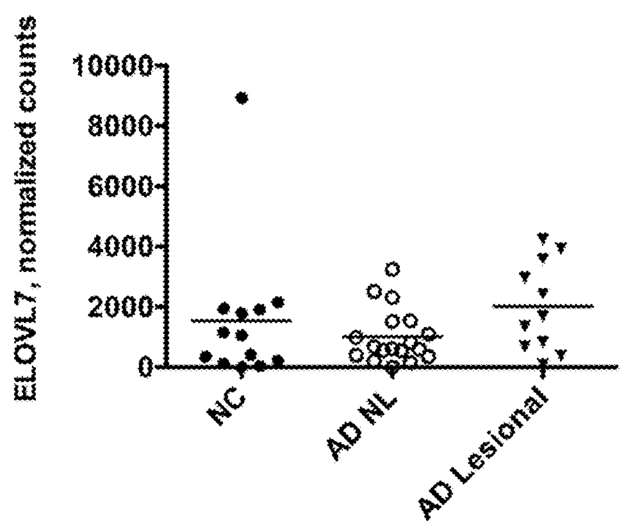

The inventors novel finding that the shift in molecular species towards shorter chain molecules in AD stratum corneum happens not only in ceramides but also in sphingomyelins and especially in lysophosphatidylcholines (LPCs) indicates a global change in fatty acid elongation. In contrast to all previous publications focused on ceramides, the inventors have included the analysis of LPC molecular species. Most LPCs are formed from its major metabolic precursor phosphatidylcholine (PC) which is the major gycerophospholipid in cells. The majority of LPC molecules formed from PC retain its sn-1 fatty acids that are incorporated into glycerol-3-phosphate and then into PC during de novo biosynthesis and therefore reflect global state of fatty acid biosynthesis and elongation rather than remodeling through Lands' cycle (Lands We. Metabolism of glycerolipides; a comparison of lecithin and triglyceride synthesis. *J Biol Chem.* 1958; 231(2):883-8). The inventors subsequent RNA-seq analysis performed on tape strips from AD and healthy subjects provides mechanistic background for the observed lipid changes by identifying decreased expression of ELOVL3 and ELOVL6 in AD lesional skin (FIGS. 3C and 3F), with concomitant increase in the expression of ELOVL1 and ELOVL4 (FIGS. 3A and 3D) thus demonstrating a compensatory response to decreased expression of ELOVL3 and ELOVL6 that only partially corrects for the insufficiency of short-chain substrates provided by ELOVL6 and long-chain fatty acids formed by ELOVL3. Previous meta-analysis combining four published AD transcriptome datasets identified wide lipid abnormalities in AD transcriptome and correlated type 2 immune activation with down-regulation of ELOVL3 and several other enzymes (Ewald D A, et al. Meta-analysis derived atopic dermatitis (MADAD) transcriptome defines a robust AD signature highlighting the involvement of atherosclerosis and lipid metabolism pathways. BMC Med Genomics. 2015; 8(60)). ELOVL3 has been previously shown to be important for a proper skin formation and functioning. ELOVL3 knockout mice exhibit a severe defect in water repulsion and increased transepidermal water loss (Westerberg R, et al. Role for ELOVL3 and fatty acid chain length in development of hair and skin function. *J Biol Chem.* 2004; 279(7):5621-9). These mice display a sparse hair coat with hyperplastic pilosebaceous system and disturbed hair lipid content with exceptionally high levels of eicosenoic acid (20:1). In the skin of these mice, the triglyceride fraction with fatty acids longer than 20 carbon atoms was almost undetectable (Westerberg R, et al. 2004). In addition, it has been shown that ELOVL3-synthesized C18:1 and C20:1 fatty acids act as agonists of peroxisome proliferator-activated receptor (PPAR)γ, master transcriptional factor regulator involved in lipid metabolism (Kobayashi T, and Fujimori K. Very long-chain-fatty acids enhance adipogenesis through coregulation of Elov13 and PPARgamma in 3T3-L1 cells. *Am J Physiol Endocrinol Metab.* 2012; 302(12):E1461-71).

Figure 8A:
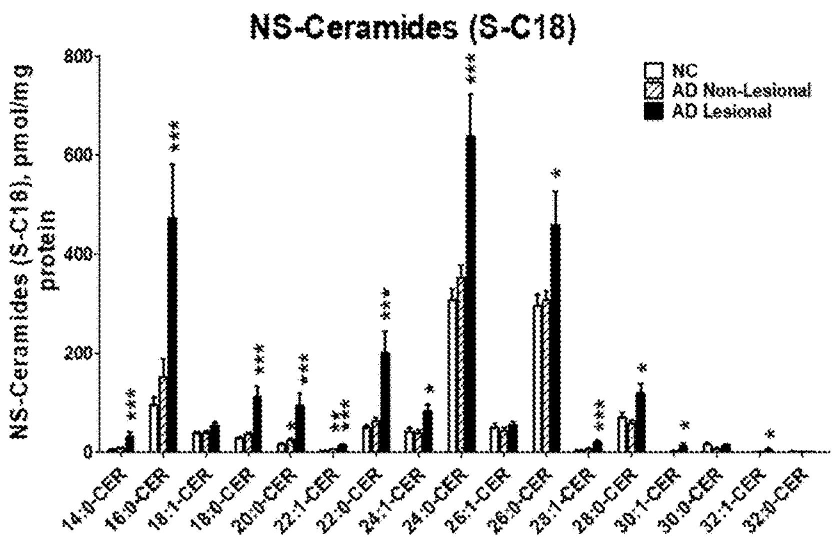
FIGS. 8A-8C show the changes in the absolute level of short- and long-chain molecular species in ceramides (FIG. 8A), sphingomyelins (FIG. 8B), and LPC (FIG. 8C) in stratum corneum of AD patients. Each lipid molecular specie was quantified by targeted LC-ESI-MS/MS and normalized by sample total protein content. Note that total level of lysophosphatidylcholines does not change, however the redistribution of the amounts of short and long-chain species is observed, this process is already pronounced in AD non-lesional skin. *p<0.5, p<0.01, *p<0.001 as compared to NC. AD lesional skin—n=15, AD non-lesional skin—n=30, NC skin—n=25.
Figure 8B:
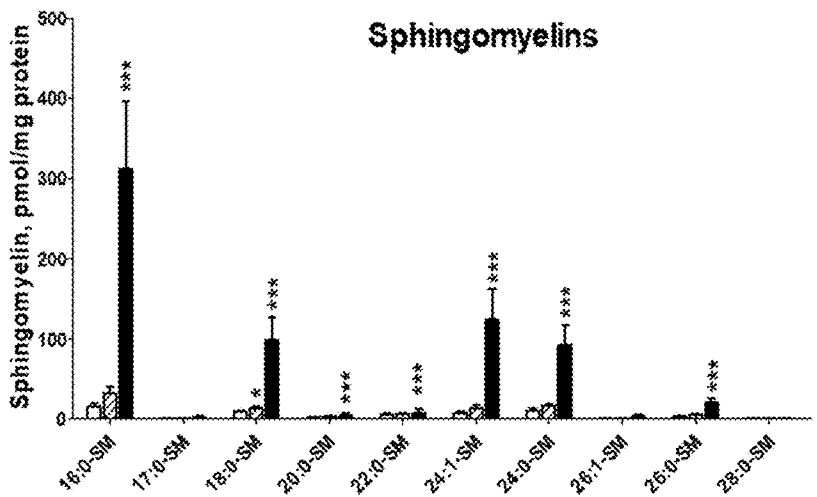

Striking similarity of lipid changes in stratum corneum between human AD subjects and induced IL-13-TG mice strongly supports the fundamental role of type 2 cytokine signaling in modifying lipid metabolism in the skin in a way that decreases stratum corneum overall hydrophobicity and barrier properties. The inventors have also made the novel finding that there is a substantial increase in total content of sphigomyelins in stratum corneum (FIG. 8B). The inventors have previously demonstrated that IL-4/IL-13 mediated elevation of sphingomyelin levels in keratinocyte membranes made keratinocytes more susceptible to binding of staphylococcal alpha toxin, thus enhancing cytolytic effects of alpha toxin in these cells (Brauweiler A M, et al. Th2 cytokines increase *Staphylococcus aureus* alpha toxin-induced keratinocyte death through the signal transducer and activator of transcription 6 (STAT6). *J Invest Dermatol.* 2014; 134(8):2114-21). Therefore, in a clinical setting, the increase in sphingomyelin (SM) content in keratinocytes in skin will favor *S. aureus* virulence, thus, contributing to *S. aureus* induced complications of AD.

Decreased acid sphingomyelinase (aSMase) activity was previously reported in AD skin (Jensen J M, et al. Impaired sphingomyelinase activity and epidermal differentiation in atopic dermatitis. *J Invest Dermatol.* 2004; 122(6):1423-31). The inventors have previously determined that aSMase localizes in punctuate granules in differentiated keratinocytes consistent with its association with lamellar bodies and observed a reduction in lamellar body formation and diffused aSMase staining in IL-4/IL-13 treated keratinocytes (Brauweiler A M, 2014).

Niemann-Pick patients with severe aSMase deficiency (i.e., <2% residual activity) demonstrate abnormal permeability barrier homeostasis, i.e. delayed recovery kinetics following acute barrier disruption by tape stripping (Schmuth M, et al. Permeability barrier disorder in Niemann-Pick disease: sphingomyelin-ceramide processing required for normal barrier homeostasis. *J Invest Dermatol.* 2000; 115(3):459-66). Delays in barrier recovery can be overridden by co-applications of topical ceramide, demonstrating that an alteration of the ceramide/sphingomyelin ratio, rather than just sphingomyelin accumulation, is likely responsible for the barrier abnormalities that occur with aSMase deficiency. These studies emphasize the importance for enzymatic processing of sphingomyelin to ceramide by aSMase as a mechanism for generating a portion of the stratum corneum ceramides for permeability barrier homeostasis in the skin (Schmuth M, et al. 2000).

Studies on permeability and biophysics of artificial lipid membranes have shown that short chain ceramides increase the permeability of the lipid membranes compared to long chain ceramides (Skolova B, et al. Ceramides in the skin lipid membranes: length matters. *Langmuir.* 2013; 29(50): 15624-33). Membranes generated from ceramides with long acyl chains formed tightly packed impermeable lipid lamellae (Skolova B, et al. 2013). Membranes containing N-16:0-NS ceramide were significantly more permeable to water (by 38-53%), theophylline (by 50-55%) and indomethacin (by 83-120%) than those containing the very long N-24:0-NS ceramide. N-24:0-NS ceramide membranes were more condensed than membranes enriched for N-16:0-NS ceramide (Pullmannova P, et al. Permeability and microstructure of model stratum corneum lipid membranes containing ceramides with long (C16) and very long (C24) acyl chains. *Biophys Chem.* 2017; 224(20-31). In the membranes composed of ceramide/free fatty acids/cholesterol sulfate partial or full replacement of ceramide by sphingomyelin increased water loss, while the permeability barrier to exogenous compounds was less sensitive to the presence of sphingomyelin (Pullmannova P, et al. Effects of sphingomyelin/ceramide ratio on the permeability and microstructure of model stratum corneum lipid membranes. *Biochim Biophys Acta.* 2014; 1838(8):2115-26). Therefore a reduction of ceramide chain length and concomitant increase in sphingomyelin content in AD skin and skin of IL-13-TG mice can result in enhanced transepidermal water loss and penetration of allergens into the skin.

Figure 6A:
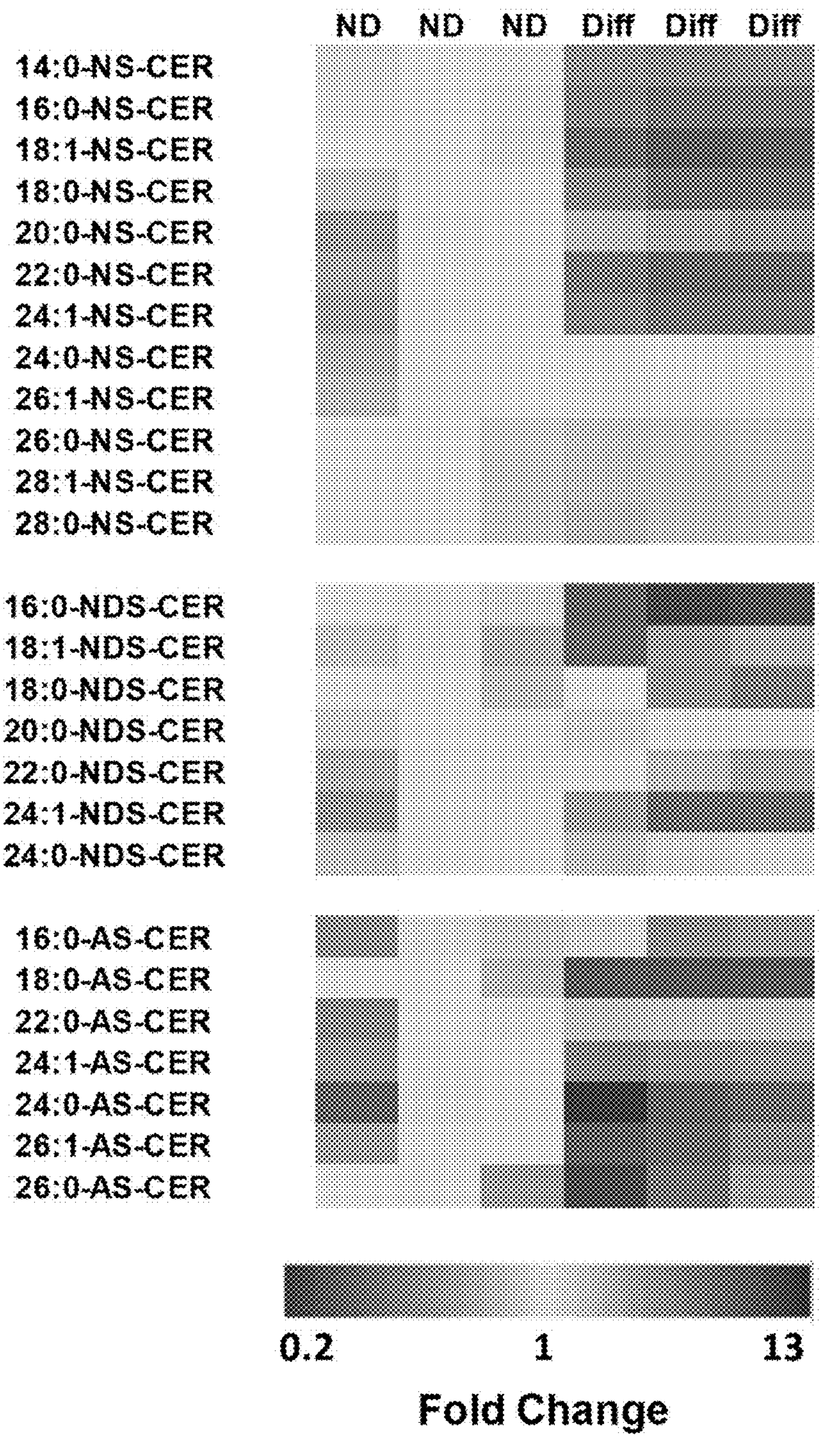
FIGS. 6A-6D show the effect of differentiation and type 2 cytokines on keratinocyte lipids.
Figure 6B:
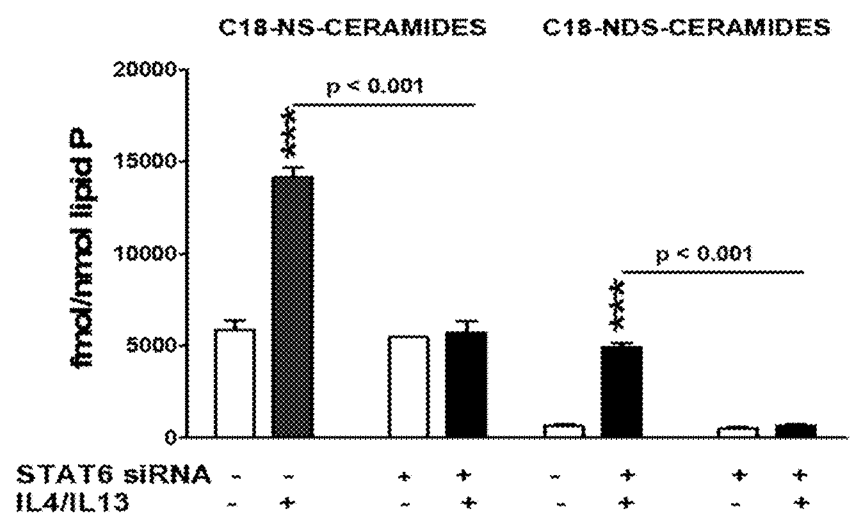
Figure 6C:
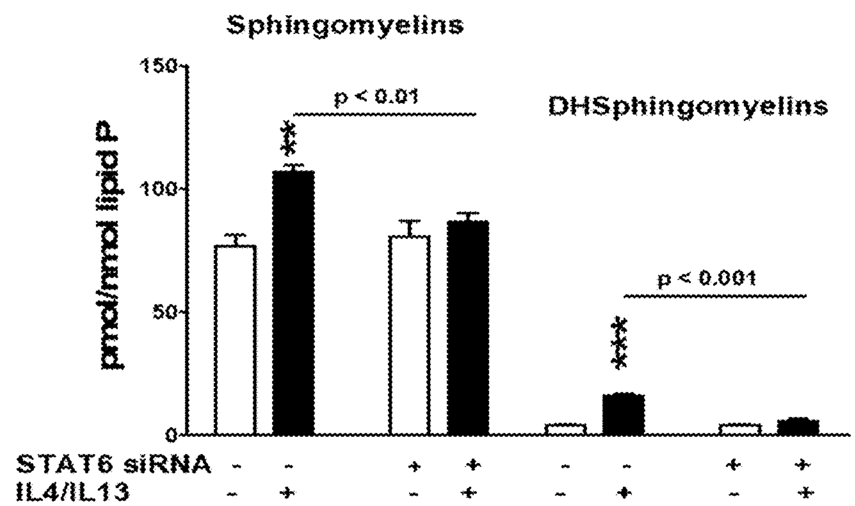

Using an in vitro keratinocyte model system, the inventors were able to recapitulate main observations from their in vivo studies using $Ca^{2+}$-differentiated human keratinocytes in vitro. Most importantly, the inventors have demonstrated critical importance of STAT6-mediated signaling in conveying IL-4/IL-13 effect on keratinocyte sphingolipids (FIG. 6C). It should be noted that while promoting changes in ceramides and sphingomyelin, IL-4/IL-13 did not affect LPC molecular species composition in differentiated keratinocytes. The inventors have also demonstrated inhibition of ELOVL3 and ELOVL6 by IL-4/IL-13 in keratinocyte cultures (FIGS. 7A-7F). Regardless of current limitations, the in vitro keratinocyte model allows for analyzing major signaling pathways involved in regulation of sphingolipid metabolism by type 2 cytokines.

Studies by the inventors and others have demonstrated that IL-4 and IL-13 are important for the pathological events that lead to AD, including the inhibition of expression of epidermal barrier proteins, FLG, involucrin (IVOL), loricrin (LOR), and others (Howell M D. Et al. 2007; Kim B E, et al. Loricrin and involucrin expression is down-regulated by Th2 cytokines through STAT-6. *Clin Immunol.* 2008; 126 (3):332-7). The importance of the IL-4 and IL-13 pathway in severe AD was demonstrated by the recent observation that blocking the IL-4Ralpha pathway with DUPILUMABD® leads to significant clinical improvement in severe AD (Simpson E L, et al. 2016; Beck L A, et al. Dupilumab treatment in adults with moderate-to-severe atopic dermatitis. *N Engl J Med.* 2014; 371(2): 130-9).

As provided for in the Examples, disclosed herein type 2 cytokines globally change lipid metabolism in the skin and reduce their carbon chain length by altering the expression of a number of enzymes involved in fatty acid elongation and sphingolipid metabolism. These alterations in skin lipidome are detrimental to the skin barrier function and illustrate a novel pathogenic function of IL-4/IL-13 activation in AD.

To establish a primary prevention strategy and/or treatment strategy for allergic diseases, it is important to identify biomarkers that can predict the occurrence of allergic diseases such as AD, food allergies, asthma and allergic rhinitis, as well as, to identify subjects having AD and one or more food allergies and subjects having AD without having a food allergy as well. The results disclosed herein demonstrate that the level of one or more lipids of skin epidermal lipids disclosed herein determined by a tape stripping method (also referred to as "skin taping") can be used as biomarkers that are predictive of allergic disease development. In addition, the lipid profile (the content and amount of two or more lipids) can be be used. In one aspect, the level and/or the relative percentage of short chain molecular species and/or the long chain molecular species of at least one lipid as disclosed herein can be determined by a method comprising mass spectrometry or mass spectrometry itself. In addition, changes in the expression of enzymes involved in skin epidermal lipid metabolism can also be determined.

The skin epidermal lipids can be ceramides, lysophosphatidylcholines, sphingomyelins, free fatty acids, and sphinogid bases. Ceramides are N-acylated sphingoid bases and include dihydrosphingosine (C18) (DS); sphingosine (C18) (S); phytosphingosine (C18) (P); 6-OH-sphingosine (C18) (H). As used herein, short chain molecular species of a lipid(s) are the species that have fatty acids with no more than 22 carbon atoms. Long chain molecular species of a lipid(s) are the species that have fatty acids with more than 22 carbon atoms.

Examples of lipids with short chain fatty acids can include:
1-O-palmitoyl-sn-glycero-3-phosphocholine (16:0-LPC);
1-O-stearoyl-sn-glycero-3-phosphocholine (18:0-LPC);
1-O-oleoyl-sn-glycero-3-phosphocholine (18:1-LPC);
1-O-linoleoyl-sn-glycero-3-phosphocholine (18:2-LPC)
Sphingosine;
N-palmitoylsphingosine (16:0-ceramide); and
N-palmitoylsphingosylphosphorylcholine (16:0-sphingomyelin).

Examples of lipids with long chain fatty acids can include:
1-O-lignoceroyl-sn-glycero-3-phosphocholine (24:0-LPC);
1-O-cerotoyl-sn-glycero-3-phosphocholine (26:0-LPC);
N-nervonoylsphingosine (24:1-ceramide);
N-lignoceroylsphingosine (24:0-ceramide);
N-cerotoylsphingosine (26:0-ceramide);
N-montanoylsphingosine (28:0-ceramide);
N-melissoylsphingosine (30:0-ceramide);
N-lignoceroylsphingosylphosphorylcholine (24:0-sphingomyelin).

Examples of lipids with ultra-long-chain fatty acid derivatives such as O-esterified ceramides (EOS) (belonging to the lipids with long chain fatty acids) can include:
CER[E(18:2)O(30)S(18)];
CER[E(18:2)O(32)S(18)];
CER[E(18:2)O(30) S(20)];
CER[E(18:2)O(32)S(20)];
CER[E(18:2)O(30)S(22)]; and
CER[E(18:2)O(32) S(22)].

Based on the inventor's findings, the proportion of short chain lysophosphatidylcholines (LPC) and 16:0-sphingomyelin (both never reported as biomarkers of atopic skin) is increased in the skin of atopic patients even in non-lesional skin while the proportion of long-chain LPC is decreased. EOS ceramides can be considered the markers of healthy skin.

One embodiment of the invention, is a method to identify a subject at risk of developing an allergic disease. The method comprises obtaining at least one skin sample from the subject and determining the level and/or percentage of short chain and long chain molecular species of at least one lipid in the skin sample. The method further comprises comparing the level and/or the relative percentage of the short and long chain molecular species of the at least one lipid in the skin sample to the same short and long chain molecular species from a healthy control sample. The subject is identified as at risk of developing an allergic disease when the level and/or the relative percentage of the short chain molecular species from the subject's sample is elevated as compared to the same short chain molecular species from the healthy control; and when the level and/or the relative percentage of the long chain molecular species from the subject's sample is decreased as compared to the same long chain molecular species from the healthy control.

Another embodiment of the invention, is a method of diagnosing and treating an allergic disease in an asymptomatic subject. The method comprises obtaining at least one skin sample from the subject and determining the level and/or percentage of short chain and long chain molecular species of at least one lipid in the skin sample. The method further comprises comparing the level and/or the relative percentage of the short and long chain molecular species of the at least one lipid in the skin sample to the same short and long chain molecular species from a healthy control sample. The subject is identified as having an allergic disease when the level and/or the relative percentage of the short chain molecular species from the subject's sample is elevated as compared to the same short chain molecular species from the healthy control; and when the level and/or the relative percentage of the long chain molecular species from the subject's sample is decreased as compared to the same long chain molecular species from the healthy control. Further, the subject is administered an effective amount of a therapeutic prior to the development of allergic disease symptoms.

In another embodiment of the methods of the invention, the methods can further comprise determining the expression level of one or more lipid metabolism enzymes in the least one skin sample from the subject and in the healthy control sample. In one aspect, the one or more lipid metabolism enzymes can be elongation of long chain fatty acids family member 1 (ELOVL1), elongation of long chain fatty acids family member 1 (ELOVL1), elongation of long chain fatty acids family member 2 (ELOVL2), elongation of long chain fatty acids family member 3 (ELOVL3), elongation of long chain fatty acids family member 4 (ELOVL4), elongation of long chain fatty acids family member 5 (ELOVL5), elongation of long chain fatty acids family member 6 (ELOVL6), elongation of long chain fatty acids family member 7 (ELOVL7), and/or combinations thereof. In a preferred embodiment, the expression levels of ELOVL3 and ELOVL6 from the skin sample is decreased as compared to the expression levels of ELOVL3 and ELOVL6 from the healthy control sample.

In still other embodiments, the methods can be used to identify, diagnose and/or treat a subject having AD and a food allergy. In yet another embodiment, the methods can be used to identify, diagnose and/or treat a subject having AD without also having a food allergy. The inventors have made the surprising finding that the skin samples from the stratum corneum from non-lesional skin of subjects with AD and food allergy differs from healthy control subjects in total content of lysophosphatidylcholines. In addition, skin samples from the Stratum corneum from non-lesional skin from subjects with AD and food allergy differs from subjects with AD without food allergy in relative percentage of lignoceroyl lysophosphatidylcholine; same for melissoyl lysophosphatidylcholine.

In one aspect of the invention, the subject is human, and in a preferable aspect the human is a human infant. Infant as used herein is defined as up to two years (24 months) of age. In addition, an asymptomatic subject, is a subject that is not producing or showing symptoms of an allergic disease. For example, an AD asymptomatic subject is a subject that is not producing or showing symptoms of AD such as, itching; red to brownish-grey patches on the skin (especially on the hands, feet, ankles, wrists, neck, upper chest, eyelids, inside the bend of the elbows and knees, face and scalp); small, raised bumps which can leak fluid and crust over when scratched; thickened, cracked, dry, scaly skin; and raw, sensitive, swollen skin from scratching. Most often, AD begins before age 5 and may persist into adolescence and adulthood. For some AD subjects, it flares up periodically and then clears up for a time.

In one aspect, once an asymptomatic subject is diagnosed as having an allergic disease, treatment can commence immediately to reduce the severity and/or delay the onset of symptoms.

In one aspect of the invention, the allergic disease can be AD, eczema, food allergy, asthma, and/or allergic rhinitis. In one embodiment, the subject can have AD with also having a food allergy. In yet another embodiment, the subject can have AD without also having a food allergy. The methods of the present invention can be used distinguish those subjects who have AD with a food allergy and those subjects that have AD without having a food allergy.

The term "sample" or "patient sample" or "subject sample" or "test sample" can be used generally to refer to a sample of any type which contains products that are to be evaluated by the present methods, including but not limited to, a skin sample including a skin epidermal sample, a skin sample from the stratum corneum, a sample of isolated cells, a tissue sample and/or a bodily fluid sample. The cells in the skin sample for example are not necessarily of the same type, although purification methods can be used to enrich for the type of cells that are preferably evaluated. Cells can be obtained, for example, by a tape stripping method (also referred to as "skin taping"), scraping of a tissue, and processing of a tissue sample to release individual cells. In regards removal of cells and thus lipids from the skin sample, the skin material can be removed from tape strips by scraping it out by a rubber scraper in an alcohol solution (such as 1-30%). The alcohol can be methanol, ethanol, butanol or isopropanol. Alternatively, the tape stripe material can be removed from the tape stripes by sonication in an alcohol solution as noted above. Alternatively, skin lipids can be directly extracted from tape strips by supercritical extraction. In one aspect of the invention, the skin sample can be taken from one or more sections of the subject's body, including lesional and/or non-lesional skin sections. In yet another aspect, one or more skin samples can be obtained and analyzed by the methods provided herein.

The skin epidermal lipids can be ceramides, lysophosphatidylcholines, sphingomyelins, free fatty acids, and sphinogid bases. In one aspect of invention, the short chain molecular species of at least one lipid can be short chain NS-ceramides, short chain sphingomyelins, short chain lysophosphatidylcholines, and combinations thereof. In another aspect of the invention, the long chain molecular species of at least one lipid can be long chain NS-ceramides, short chain sphingomyelins, short chain lysophosphatidylcholines, and combinations thereof.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not. This can include determining whether the gene expression is upregulated (or increased) as compared to a control, downregulated as compared to a control, or unchanged as compared to a control or increased or decreased as compared to a reference or control level. Therefore, the step of detecting or determining expression does not require that expression of the gene actually is upregulated or downregulated or increased or decreased, but rather, can also include detecting or determining that the expression of the gene has not changed (i.e., detecting no expression of the gene or no change in expression of the gene).

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), and reverse transcriptase-polymerase chain reaction (RT-PCR), quantitative PCR, and/or RNA Ampliseq, followed by quantitative detection of the product by any of a variety of means; multiplexed quantitative PCR enrichment of cDNA amplicons, followed by conversion of amplicons to sequence libraries and Next-generation based sequencing of libraries to generate digital count expression data; extraction of total RNA from the cells, which is then labeled and used to probe cDNAs or oligonucleotides encoding the gene on any of a variety of surfaces; in situ hybridization; and detection of a reporter gene.

Methods to measure protein expression levels generally include, but are not limited to: mass spectrometry, Western blot, immunoblot, enzyme-linked immunosorbant assay (ELISA), radioimmunoassay (MA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, *Anal. Biochem.* 212:457; Schuster et al., 1993, *Nature* 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR).

In one aspect of the invention, the level and/or the relative percentage of the short chain molecular species and/or the long chain molecular species of at least one lipid is determined. An elevated or decreased level parameter is used when absolute amounts of any lipid is evaluated as expressed per mg tissue protein. The relative percentage parameter is used when one compares the abundance of lipid species within its own class. For example, relative percentage of LPC-24:0 is its percentage within all LPC species. Relative percentage of NS-ceramide-24:0 is its percentage within only NS-ceramides. The sum of the absolute values for all species within its class is determined and then each value is expressed as % of the sum.

As used herein, an elevated (or increased) level means that the level is statistically higher in comparison to the same levels from health control subjects. A decreased level means that the level is statistically lower in comparison to the same levels from health control subjects.

In one aspect of the invention, the ratio between one or more short chain lipids and one or more long chain lipids is compared to the ratio of the same short and long chain lipid(s) from a healthy subject.

In one aspect of the invention, the subject identified as being at risk and/or predisposed to develop allergic disease or a subject having been diagnosed as having an allergic disease, but is asymptomatic, is administered a therapeutic. In one aspect, the therapeutic is a topical therapeutic. In one aspect, the therapeutic is a systemic therapeutic. In one aspect, the therapeutic can be administered by an administration route including oral, inhalation, parenteral, subcutaneous injection, intravenous, transdermal and combinations thereof. In one aspect, the therapeutic is a therapy that reduces type 2 immune responses for use in the prevention and/or treatment of AD in a subject in need thereof. In one aspect, the therapeutic delays the onset of symptoms of an allergic disease. In one aspect, the therapeutic can increase elongase activity in the subject. In one aspect, the therapeutic can reverse inflammation. In another aspect, the therapeutic reduces the severity of an allergic disease. In one aspect, the subject can be administered Dupilimab. In still another aspect, combinations of therapeutics can be administered to the subject.

The therapeutic can be a moisturizer (also referred to as an emollient). Moisturization prevents the skin from becoming dry. Moisturizers can be administered, hourly, daily, twice a day, three times a day or more if the skin becomes dry. Moisturizers can be in the form of lotions, creams, ointments, and/or bath/shower additives. The same or different moisturizers can be administered to the subject at the same time or at different times. For example, a thick ointment may be used as a soap substitute as normal soap tends to dry the skin out. An ointment may be administered at bedtime followed by administration of cream during the day. An ointment may be administered on some areas of the body of the subject, while a cream may be administered to other areas of the body. The moisturizer can be administered to the subject topically.

The therapeutic can be also an anti-inflammatory drug, such as a topical steroid (including corticosteroids) or calcineurin inhibitor. These anti-inflammatory drugs can be administered to the subject as a separate treatment or can be administered in conjugation with other therapeutics. For example, a moisturizer can be administered to the subject first, followed by administration of the steroid.

In one aspect of the invention, the moisturizer or anti-inflammatory drug is in a pharmaceutical composition. The composition can include a pharmaceutically acceptable carrier.

In one aspect, the anti-inflammatory drug is administered to the subject by an administration route including but not limited to topical, oral, subcutaneous administration and combinations thereof.

In one aspect of the invention, the therapeutic can be a lipid or non-lipid compound that affects biosynthesis and degradation of short-chain and long-change molecules identified as a group of lipids used in the invention. These can include ointments and non-ointment therapeutics that affect fatty acid elongases (ELOVLs) and ceramidases and can improve skin lipid composition.

In some aspects of the invention, the subjects can be treated by administration of one or more compounds including but not limited, corticosteroids, leukotriene antagonists, anti-cytokine antibodies, anti-cytokine receptor antibodies, anti-IgE antibody, anti-IL14 antibodies, anti-IL13 antibodies, JAK kinase inhibitors, JAK/STAT inhibitors, antibiotics, a phosphodiesterase inhibitor, and combinations thereof.

In still other aspects, the level and/or relative percentage of short chain molecular species and long chain molecular species of at least one lipid and/or expression of the enzymes involved in lipid metabolism of the subject can be determined and compared at 1 month of age, 2 months of age, 3 months of age, 4 months of age, 5 months of age, 6 month of age, 7 months of age, 8 months of age, 9 months of age, 10 months of age, 11, months of age, 12 months of age, 13 months of age, 14 months of age, 15 months of age, 16 months of age, 17 months of age, 18 months of age, 19 months of age, 20 months of age, 21 months of age, 22 months of age, 23 months of age or 24 months of age. The level and relative percentage can be determined for the subject at more than one age. For example, the level and relative percentage of short chain molecular species and long chain molecular species of at least one lipid can be determined at 2 months of age and then again at 6 months of age.

As used herein, reference to a reference or control, means a subject who is a relevant reference or control to the subject being evaluated by the methods of the present invention. The control can be matched in one or more characteristics to the subject. In one aspect, the control, is considered to be a healthy control and can be an individual (such as an infant) with no family history of allergy and does not develop an allergic disease such as AD. No family history of allergy indicates that both parents had neither allergy nor skin test reactivity to 8 common inhalant allergens (*Dermatophagoides pteronyssinus, D. farinae*, tree pollen mixture I & II, weed pollen mixture, grass pollen mixture, cat, and cockroach). The control level and/or the relative percentage of the short chain molecular species and/or the long chain molecular species, expression level used in the comparison of the methods of the present invention can be determined from one or more relevant reference or healthy control subjects.

Another embodiment of the present invention relates to a kit for skin tape strip collection. In one aspect, the kit comprises adhesive sampling discs, storage cards, a pressure instrument (such as a spring-loaded device providing uniform pressure), and angular tweezers (D-SQUAME®)

The following examples are provided for illustrative purposes and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Example 1

This example shows lipid abnormalities are associated with skin lesions in atopic dermatitis.

Methods: Lipid profiles from skin tape strips of 15 healthy controls, 20 AD and 5 psoriasis patients were analyzed by targeted liquid chromatography tandem mass spectrometry and lipid pathway transcriptome by RNAseq.

Results: The relative proportion of sphingolipids with long-chain fatty acids (C22-C32) was decreased in lesional AD skin (Mean±SD 73.9±4.1%, 80.4±5.5% of total ceramides for AD lesional skin and normal skin, respectively, $p<0.05$) while short-chain fatty acid sphingolipids (C14-C20) were increased in AD. A similar pattern was observed in skin free fatty acids. Parallel significant changes in the expression of enzymes involved in sphingolipid metabolism were found in AD lesional skin by RNAseq (fatty acid elongases ELOVL1, ELOVL4 (increased), ELOVL3, ELOVL6 (decreased); enzymes and regulators of de novo shingolipid biosynthesis SPTLC2 (increased), ORMDL3 (decreased); regulators of ceramide levels ceramidase ASAH1 (decreased) and sphingomyelinase SMPD1 (increased). In contrast, psoriatic skin demonstrated a relative increase of long-chain (86.1±3.8% of total ceramides, $p<0.05$ compared to normal skin) and decreased short-chain ceramides.

Conclusions:

This study identifies novel lipid changes in AD skin that can account for increased transepidermal water loss in AD skin. It is believed that sphingolipid biosynthesis and the elongation of fatty acids are metabolic processes affected by the atopic immune response. In contrast to AD, increased levels of long-chain ceramides in psoriasis skin reflect different underlying pathways.

Example 2

This example shows that human AD skin has a characteristic decrease in very long chain fatty acids within several classes of lipids.

Ceramides in the stratum corneum of AD skin undergo reduced chain length elongation of their N-linked fatty acid that can contribute to their total diminished hydrophobicity (Feingold K R, and Elias P M. Role of lipids in the formation and maintenance of the cutaneous permeability barrier. *Biochim Biophys Acta.* 2014; 1841(3):280-94). To determine if this is a global characteristic of AD skin lipids rather than a ceramide-specific phenomenon, stratum corneum ceramides as well as sphingomyelin (SM) and lysophosphatidylcholine (LPC) molecular species were anyalyzed by high performance liquid chromatography electrospray ionization tandem mass spectrometry (UHPLC-ESI-MS/MS). In this study, analysis of skin tape strips from 25 normal healthy controls, 30 AD non-lesional skin samples and 15 matching AD lesional skin samples demonstrated that AD is characterized by a global reduction in lipid molecular species with long-chain (>24 carbons) fatty acids. This phenomenon was visible not only in ceramides (in particular in NS-ceramides with C18-sphingosine as their sphingoid base, S-C18) but also in sphingomyelins and particularly in lysophosphatidylcholines (FIG. 1A-1C), a novel observation. If in ceramides the decline in long-chain NS-ceramide molecular species (C24-C28) was found to be modest (FIG. 1A), similar to sphingomyelins (C26-C28) (FIG. 1B), LPCs demonstrated a profound downregulation of molecular species with fatty acids ranging from C22 to C30 carbon atoms (FIG. 1C). Simultaneously, all studied lipids demonstrated a notable increase of molecular species with short chain fatty acids (C16-C20). This increase was visible for NS-ceramides N-acylated with C16-C22 fatty acids, sphingomyelin N-acylated with palmitic acid, and LPCs with C16-C18 fatty acids (FIG. 1A-1C). Strikingly, changes in LPC molecular species were markedly visible not only in stratum corneum collected from AD lesional skin but also in non-lesional skin of AD patients. Furthermore, the Volcano plot of changes in relative percentage of analyzed lipids within their corresponding subclasses revealed additional groups of ceramides with C20- and C22-sphingosine with alpha-hydroxy fatty acids that demonstrated significant shifts in their proportion of short-chain and long-chain alpha-hydroxy fatty acid containing species in non-lesional skin from AD patients, which continued to be strongly dysregulated in lesional skin (FIGS. 2A and 2B and Table 2).

TABLE 2

Figure 2A:
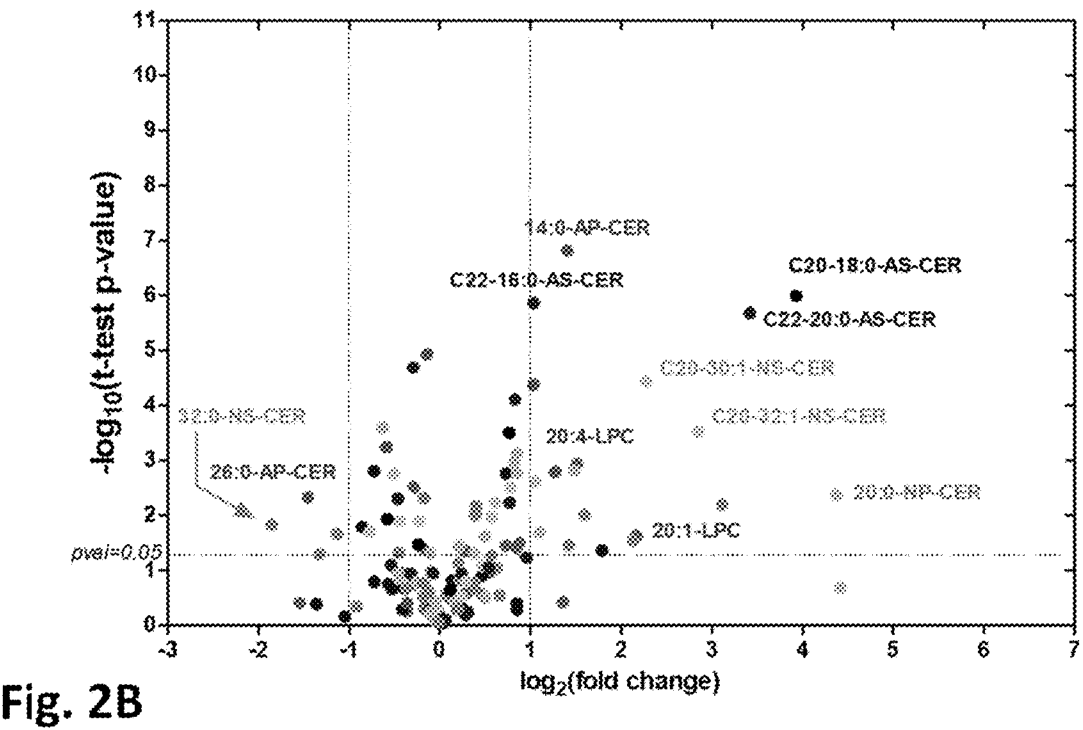
FIGS. 2A-2B show volcano plots of changes in relative percentage in molecular species of lipids from selected individual lipid subclasses in non-lesional (FIG. 2A) and lesional (FIG. 2B) stratum corneum of AD patients versus NC subjects. Each lipid molecular species was quantified by targeted or semi-targeted LC-ESI-MS/MS, normalized by sample total protein content, and data were expressed as relative percentage within each lipid subclass. Note that LPC molecular species demonstrate the most striking reciprocal shift in the long-chain and short-chain molecules in lesional AD skin. AD lesional skin—n=15, AD non-lesional skin—n=30, NC skin—n=25.
Figure 2B:
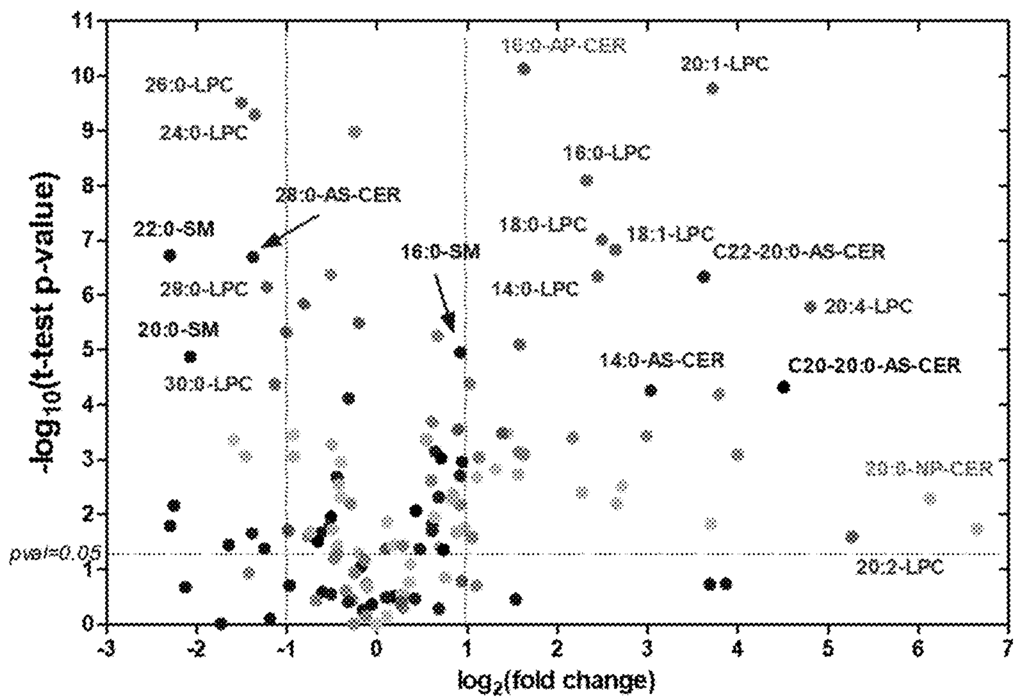

Log2 (fold change) and Log10 (p value) values of the ratios AD_Lesional/Normal Controls and AD_Non-Lesional/Normal Controls for each lipid species respresented in FIGS. 2A-2B

| | AD Lesional versus Healthy Controls | | AD Non-Lesional versus Healthy Controls | |
|---|---|---|---|---|
| Lipid Species | Log2 (Fold Change) | Log10 (p value) | Log2 (Fold Change) | Log10 (p value) |
| 14:0-LPC | 2.445 | 6.348 | 0.876 | 1.493 |
| 16:0-LPC | 2.322 | 8.100 | 0.845 | 1.406 |
| 18:0-LPC | 2.494 | 7.015 | 0.728 | 1.445 |
| 18:1-LPC | 2.643 | 6.830 | 0.559 | 0.958 |
| 18:2-LPC | 1.578 | 5.088 | −0.361 | 0.248 |
| 18:3-LPC | 0.100 | 1.381 | −1.547 | 0.409 |
| 20:0-LPC | 0.938 | 0.781 | 0.289 | 0.577 |
| 20:1-LPC | 3.717 | 9.777 | 2.174 | 1.627 |
| 20:2-LPC | 5.266 | 1.591 | 1.357 | 0.414 |
| 20:4-LPC | 4.804 | 5.784 | 1.513 | 2.932 |
| 22:0-LPC | −1.003 | 5.312 | −0.050 | 0.145 |
| 24:0-LPC | −1.354 | 9.298 | −0.188 | 1.404 |
| 26:0-LPC | −1.505 | 9.517 | −0.285 | 2.508 |
| 28:0-LPC | −1.220 | 6.152 | 0.127 | 0.649 |
| 30:0-LPC | −1.130 | 4.371 | 0.285 | 1.346 |
| 16:0-SM | 0.924 | 4.947 | 0.242 | 0.336 |
| 17:0-SM | −2.123 | 0.679 | −1.049 | 0.156 |
| 18:0-SM | −0.057 | 0.365 | −0.049 | 0.405 |
| 20:0-SM | −2.072 | 4.870 | −0.861 | 1.787 |
| 22:0-SM | −2.296 | 6.725 | −0.724 | 2.800 |
| 24:1-SM | 0.944 | 2.961 | 0.733 | 2.757 |
| 24:0-SM | −0.158 | 0.261 | 0.133 | 0.820 |
| 26:1-SM | −1.729 | 0.012 | −1.362 | 0.383 |
| 26:0-SM | −0.626 | 1.666 | −0.110 | 0.306 |
| 28:0-SM | −1.246 | 1.380 | −0.411 | 0.677 |
| DH-16:0-SM | −0.606 | 0.588 | 0.309 | 0.230 |
| DH-17:0-SM | 3.869 | 0.742 | 0.852 | 0.280 |
| DH-18:0-SM | 3.688 | 0.730 | 1.791 | 1.361 |
| DH-20:0-SM | 1.537 | 0.462 | 0.850 | 0.393 |
| DH-22:0-SM | −1.641 | 1.445 | 0.005 | 0.052 |
| DH-24:1-SM | −1.186 | 0.106 | 0.462 | 0.902 |
| DH-24:0-SM | −2.252 | 2.160 | −0.569 | 0.743 |
| DH-26:0-SM | −2.291 | 1.796 | −0.526 | 0.662 |
| 16:0-OH-SM | −0.970 | 0.712 | −0.721 | 0.788 |
| 14:0-NS-CER | 1.129 | 3.037 | 0.387 | 0.779 |
| 16:0-NS-CER | 0.920 | 2.179 | 0.391 | 0.661 |
| 18:1-NS-CER | −0.275 | 0.443 | −0.296 | 0.731 |
| 18:0-NS-CER | 0.668 | 5.256 | 0.122 | 0.466 |
| 20:0-NS-CER | 1.027 | 4.380 | 0.396 | 2.031 |
| 22:1-NS-CER | 1.574 | 3.129 | 0.462 | 0.568 |
| 22:0-NS-CER | 0.609 | 3.681 | 0.202 | 1.126 |
| 24:1-NS-CER | −0.120 | 0.155 | −0.375 | 0.667 |
| 24:0-NS-CER | −0.120 | 0.738 | 0.074 | 0.554 |
| 26:1-NS-CER | −0.762 | 1.600 | −0.411 | 0.964 |
| 26:0-NS-CER | −0.429 | 2.635 | −0.043 | 0.123 |
| 28:1-NS-CER | 0.549 | 3.354 | 0.394 | 1.996 |
| 28:0-NS-CER | −0.343 | 0.607 | −0.448 | 1.316 |
| 30:1-NS-CER | 2.987 | 3.429 | 1.598 | 1.998 |
| 30:0-NS-CER | −0.676 | 0.438 | −1.329 | 1.290 |
| 32:1-NS-CER | 3.995 | 3.089 | 2.131 | 1.542 |
| 32:0-NS-CER | −1.420 | 0.931 | −1.853 | 1.822 |
| 16:0-NDS-CER | 0.698 | 1.393 | −0.170 | 0.300 |
| 18:1-NDS-CER | −0.246 | 8.986 | −1.136 | 1.659 |
| 18:0-NDS-CER | 0.291 | 0.294 | −0.166 | 0.351 |
| 20:0-NDS-CER | 0.599 | 2.615 | 0.215 | 0.822 |
| 22:0-NDS-CER | −0.296 | 2.193 | −0.064 | 0.397 |
| 24:1-NDS-CER | 1.625 | 3.090 | 0.625 | 1.042 |
| 24:0-NDS-CER | −0.516 | 6.378 | −0.176 | 2.314 |
| 26:1-NDS-CER | 1.099 | 0.702 | 0.661 | 0.545 |
| 26:0-NDS-CER | 0.298 | 0.506 | 0.564 | 1.258 |
| 28:1-NDS-CER | | | | |
| 28:0-NDS-CER | 2.167 | 3.397 | 1.424 | 1.451 |
| 30:1-NDS-CER | −0.257 | 0.007 | −0.914 | 0.337 |
| 30:0-NDS-CER | 3.791 | 4.189 | 3.113 | 2.187 |
| 14:0-AS-CER | 3.032 | 4.258 | 0.956 | 1.230 |
| 16:0-AS-CER | 0.646 | 3.150 | 0.244 | 0.932 |
| 18:0-AS-CER | −0.322 | 0.413 | −0.541 | 1.094 |
| 20:0-AS-CER | 0.612 | 1.832 | 0.062 | 0.098 |
| 22:0-AS-CER | 0.475 | 1.373 | 0.042 | 0.046 |
| 24:1-AS-CER | 0.688 | 0.288 | −0.116 | 0.279 |

TABLE 2-continued

Log2 (fold change) and Log10 (p value) values of the ratios AD_Lesional/Normal Controls and AD_Non-Lesional/Normal Controls for each lipid species respresented in FIGS. 2A-2B

| | AD Lesional versus Healthy Controls | | AD Non-Lesional versus Healthy Controls | |
|---|---|---|---|---|
| Lipid Species | Log2 (Fold Change) | Log10 (p value) | Log2 (Fold Change) | Log10 (p value) |
| 24:0-AS-CER | −0.176 | 1.044 | −0.013 | 0.218 |
| 26:1-AS-CER | −0.510 | 0.550 | 0.299 | 0.215 |
| 26:0-AS-CER | −0.443 | 2.690 | −0.040 | 0.233 |
| 28:1-AS-CER | −1.385 | 1.658 | 0.276 | 0.190 |
| 28:0-AS-CER | −1.376 | 6.700 | −0.463 | 2.298 |
| C20-14:0-NS-CER | 0.360 | 0.765 | 0.783 | 2.505 |
| C20-16:0-NS-CER | 0.111 | 0.153 | 0.239 | 0.520 |
| C20-18:1-NS-CER | 0.368 | 1.097 | 0.613 | 2.229 |
| C20-18:0-NS-CER | 1.110 | 2.678 | 0.572 | 1.964 |
| C20-20:0-NS-CER | 0.641 | 1.955 | 0.385 | 1.307 |
| C20-22:0-NS-CER | 0.176 | 0.453 | 0.291 | 0.792 |
| C20-24:1-NS-CER | −0.007 | 0.003 | −0.033 | 0.068 |
| C20-24:0-NS-CER | 0.181 | 1.437 | 0.213 | 1.444 |
| C20-26:1-NS-CER | −0.400 | 2.311 | −0.506 | 2.748 |
| C20-26:0-NS-CER | 0.109 | 1.860 | −0.028 | 0.320 |
| C20-28:1-NS-CER | 1.315 | 2.831 | 1.052 | 2.604 |
| C20-28:0-NS-CER | −0.402 | 2.955 | −0.227 | 1.892 |
| C20-30:1-NS-CER | 2.716 | 2.522 | 2.279 | 4.427 |
| C20-30:0-NS-CER | −0.924 | 3.449 | −0.444 | 1.891 |
| C20-32:1-NS-CER | 3.701 | 1.828 | 2.851 | 3.522 |
| C20-32:0-NS-CER | −1.587 | 3.354 | −0.773 | 1.708 |
| C20-14:0-AS-CER | | | −0.010 | 0.042 |
| C20-16:0-AS-CER | −0.656 | 1.517 | 0.766 | 3.501 |
| C20-18:0-AS-CER | 0.713 | 3.029 | 3.932 | 5.990 |
| C20-20:0-AS-CER | 4.506 | 4.321 | 0.195 | 0.291 |
| C20-22:0-AS-CER | 0.740 | 1.355 | 0.116 | 0.635 |
| C20-24:0-AS-CER | 0.433 | 2.070 | −0.235 | 1.466 |
| C20-26:0-AS-CER | 0.190 | 0.512 | −0.580 | 1.927 |
| C20-28:0-AS-CER | −0.511 | 1.966 | | |
| C22-14:0-NS-CER | 0.964 | 1.740 | 0.158 | 0.407 |
| C22-16:0-NS-CER | 1.439 | 3.477 | 0.820 | 2.963 |
| C22-18:1-NS-CER | 0.877 | 1.674 | 0.850 | 2.765 |
| C22-18:0-NS-CER | 1.564 | 2.730 | 0.852 | 3.120 |
| C22-20:0-NS-CER | 0.836 | 2.278 | 0.477 | 1.075 |
| C22-22:0-NS-CER | 0.844 | 2.379 | 0.499 | 1.622 |
| C22-24:1-NS-CER | 0.268 | 0.554 | −0.110 | 0.237 |
| C22-24:0-NS-CER | 0.539 | 3.373 | 0.209 | 1.413 |
| C22-26:1-NS-CER | −0.500 | 3.266 | −0.633 | 3.592 |
| C22-26:0-NS-CER | −0.104 | 0.670 | −0.100 | 0.977 |
| C22-28:0-NS-CER | −0.425 | 2.545 | −0.106 | 1.307 |
| C22-30:0-NS-CER | −0.921 | 3.054 | −0.163 | 0.747 |
| C22-32:0-NS-CER | −1.457 | 3.065 | −0.441 | 0.848 |
| C22-14:0-AS-CER | 0.419 | 0.467 | 0.771 | 2.231 |
| C22-16:0-AS-CER | 0.609 | 1.701 | 1.035 | 5.855 |
| C22-18:0-AS-CER | 0.684 | 2.311 | 0.829 | 4.105 |
| C22-20:0-AS-CER | 3.622 | 6.341 | 3.417 | 5.674 |
| C22-22:0-AS-CER | 0.920 | 2.707 | 0.540 | 1.049 |
| C22-24:0-AS-CER | 0.103 | 0.492 | −0.073 | 0.946 |
| C22-26:0-AS-CER | −0.312 | 4.115 | −0.294 | 4.688 |
| C22-28:0-AS-CER | −0.525 | 1.772 | −0.322 | 0.935 |
| 14:0-NP-CER | 6.652 | 1.736 | 4.422 | 0.681 |
| 16:0-NP-CER | 2.658 | 2.198 | 1.484 | 2.814 |
| 18:0-NP-CER | 0.756 | 0.849 | 0.504 | 0.501 |
| 20:0-NP-CER | 6.130 | 2.289 | 4.373 | 2.361 |
| 22:0-NP-CER | 2.270 | 2.404 | 1.100 | 1.687 |
| 24:0-NP-CER | −0.201 | 1.293 | −0.052 | 0.422 |
| 26:0-NP-CER | −0.442 | 1.433 | −0.089 | 0.174 |
| 28:0-NP-CER | −0.494 | 1.726 | −0.257 | 0.796 |
| 30:0-NP-CER | −0.733 | 1.680 | −0.460 | 0.948 |
| 16:0-AP-CER | 1.630 | 10.136 | 1.035 | 4.376 |
| 18:0-AP-CER | 0.899 | 3.547 | −0.361 | 0.411 |
| 20:0-AP-CER | 0.270 | 0.402 | 1.273 | 2.789 |
| 22:0-AP-CER | 1.387 | 3.479 | −0.140 | 4.928 |
| 24:0-AP-CER | −0.203 | 5.487 | −0.587 | 3.239 |
| 26:0-AP-CER | −0.809 | 5.836 | −1.454 | 2.320 |
| 28:0-AP-CER | −0.981 | 1.716 | | |
| EO30S18 | 0.287 | 1.434 | −0.181 | 0.524 |
| EO32S18 | 1.057 | 1.580 | −0.185 | 0.758 |
| EO30S20 | −0.249 | 0.939 | −0.010 | 0.052 |
| EO32S20 | −0.135 | 1.175 | −0.121 | 0.594 |

TABLE 2-continued

Log2 (fold change) and Log10 (p value) values of the ratios AD_Lesional/Normal Controls and AD_Non-Lesional/Normal Controls for each lipid species respresented in FIGS. 2A-2B

| | AD Lesional versus Healthy Controls | | AD Non-Lesional versus Healthy Controls | |
|---|---|---|---|---|
| Lipid Species | Log2 (Fold Change) | Log10 (p value) | Log2 (Fold Change) | Log10 (p value) |
| EO30S22 | −0.467 | 1.203 | 0.400 | 2.167 |
| EO32S22 | −0.445 | 1.274 | 0.203 | 0.297 |

Figure 8C:
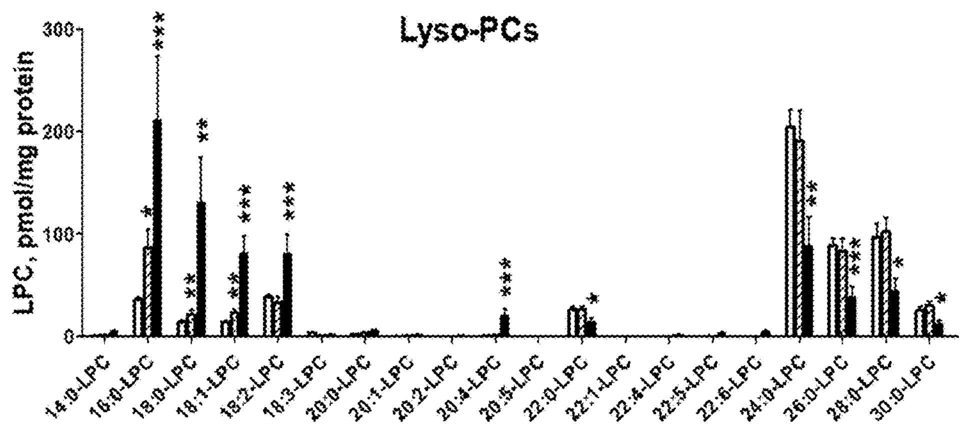

In addition, total absolute amounts of sphingomyelins (FIG. 8B) and NS-ceramides (FIG. 8A) were substantially increased in AD lesional skin when normalized per total sample protein content, while total LPC content normalized per total sample protein content did not change due to simultaneous up- and down-regulation of individual LPC molecular species (FIG. 8C).

Figure 9A:
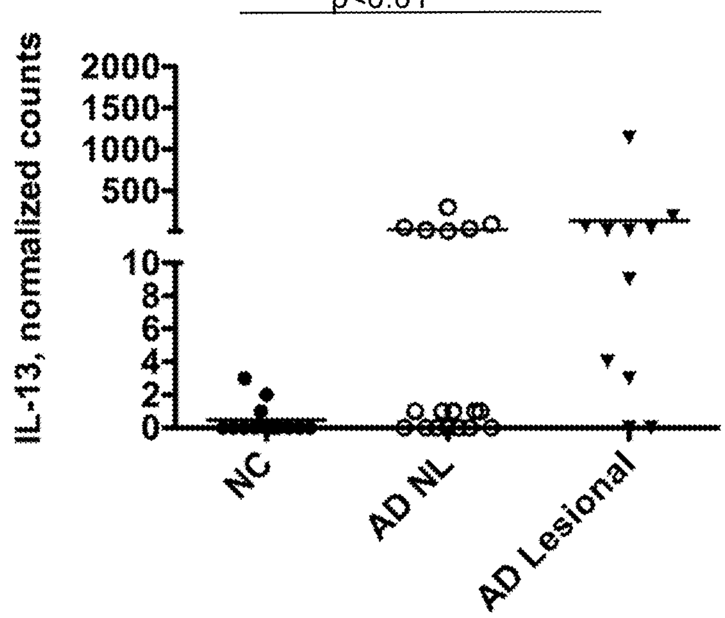
FIGS. 9A and 9B show increased expression of IL-13 (FIG. 9A) and IL-4R (FIG. 9B) in skin tape strip RNA samples collected from AD lesional and AD non-lesional skin as detected by RNAseq analysis of the skin tape strips. AD lesional skin—n=12, AD non-lesional skin—n=18, NC skin—n=13.
Figure 9B:
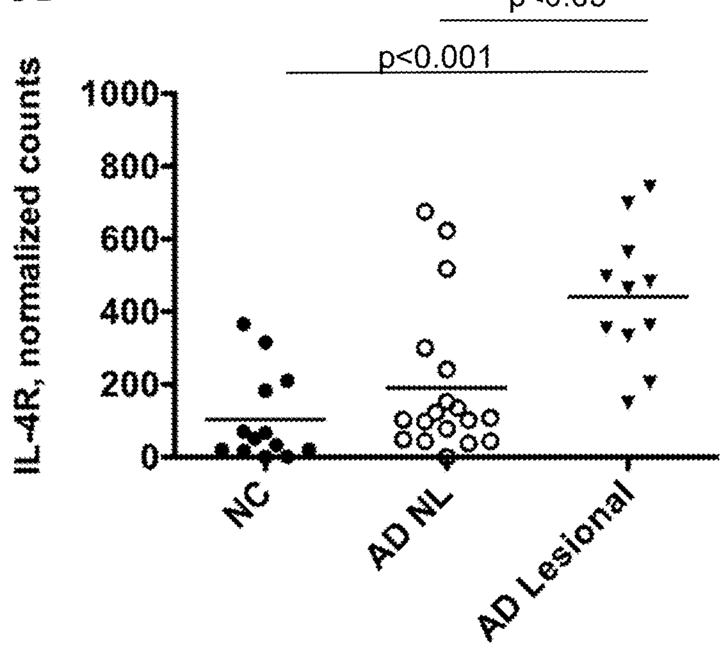

In view of the fact that stratum corneum lipids in AD skin have a clear shift in fatty acids associated not only with sphingolipids but also with glycerolipids towards the prevalence of species with short-chain fatty acids, skin tape strips collected from these patients was analyzed by RNA sequencing for the expression of enzymes that are involved in fatty acid elongation, elongation of long chain fatty acids family members 1-7 (ELOVL1-7). FIGS. 3A-3G demonstrates that lesional AD skin has diminished expression of ELOVL3 and ELOVL6. ELOVL3 is responsible for the formation of long-chain (C18-C24) fatty acids from their short-chain precursors, while ELOVL6 forms short-chain fatty acids (C12-C18). At the same time, the expression of ELOVL1 and ELOVL4 that form predominantly very long-chain fatty acids was increased. Thus, RNAseq analysis of human tape strips revealed a shift in the expression pattern of enzymes that elongate short- and long-chain fatty acids in lesional AD skin. At the same time RNAseq analysis of skin tape strip samples demonstrated increased expression of IL-13 in non-lesional AD skin (FIG. 9A), and more so in lesional AD skin, which was also accompanied by the upregulation of IL-4R expression in these samples (FIG. 9B).

Example 3

This example shows lipid changes in skin tape strips from IL-13 transgenic mice recapitulate lipid phenotype observed in human AD lesional skin.

Figure 4A:
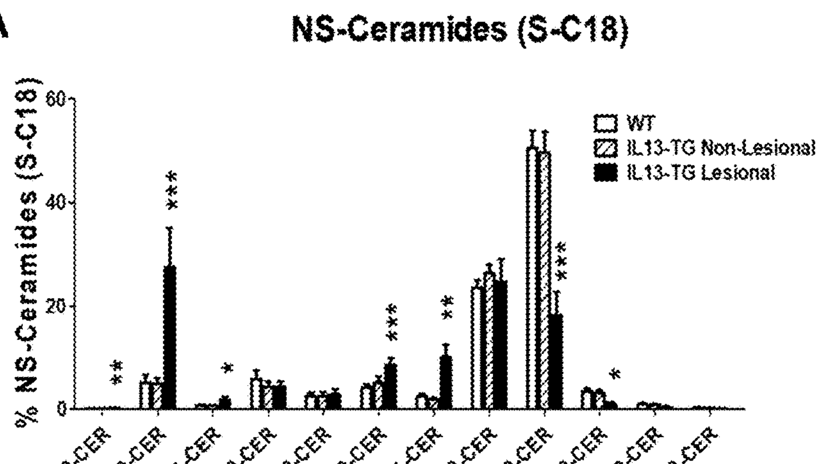
FIGS. 4A-4C show changes in relative level of short- and long-chain molecular species in ceramides (FIG. 4A), sphingomyelins (FIG. 4B), and lysophosphatidylcholines (FIG. 4C) in stratum corneum from non-lesional and lesional skin of IL-13-TG mice and their littermate controls. IL-13-TG mice spontaneously develop skin lesions. Tape strips were collected from both lesional and non-lesions areas of mouse skin. Each lipid molecular specie was quantified by targeted LC-ESI-MS/MS, normalized by sample total protein content, and data were expressed as relative percentage within each lipid subclass. *p<0.05, p<0.01, *p<0.001 versus wild type littermate control, n=6-10.
Figure 4B:
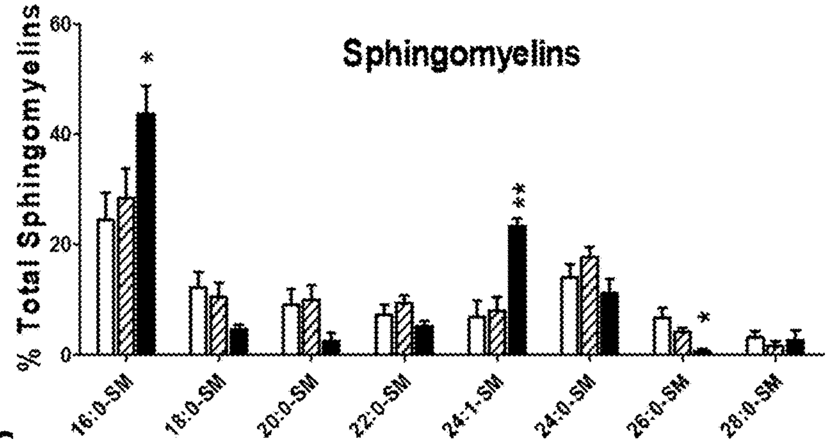
Figure 4C:
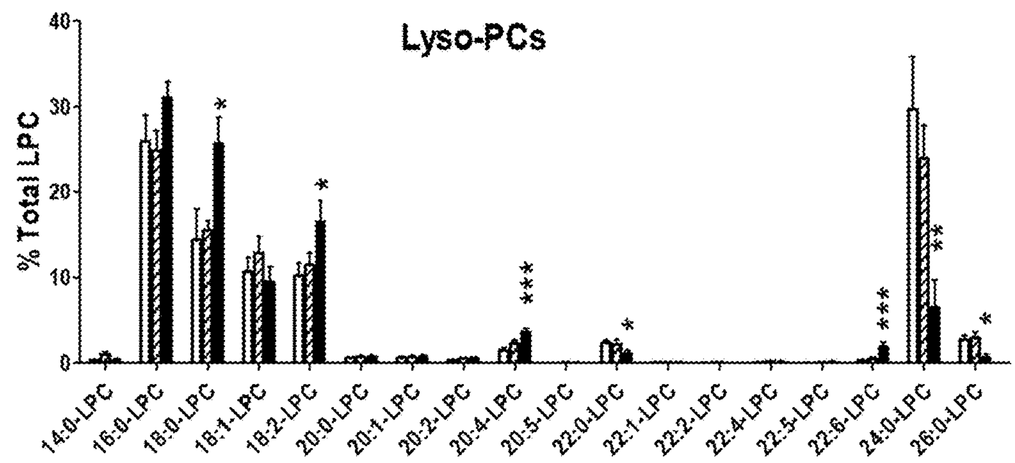

K5-tTA-IL-13 transgenic (IL-13-TG) mice have been previously developed (Zheng T, et al. Transgenic expression of interleukin-13 in the skin induces a pruritic dermatitis and skin remodeling. *J Invest Dermatol.* 2009; 129(3):742-51; Oh M H, et al. IL-13 induces skin fibrosis in atopic dermatitis by thymic stromal lymphopoietin. *J Immunol.* 2011; 186(12): 7232-42). In these mice, IL-13 expression is driven by a keratinocyte-specific promoter upon removal of doxycycline (DOX). As a result, these mice spontaneously develop severe atopic skin lesions 2-4 months after the induction of IL-13 expression in the skin and therefore provide a good model for AD development in humans. Skin tape strip samples were analyzed from six animals that developed AD lesions, eight non-lesional areas from animals that either developed skin lesions (6 animals) or did not develop lesions within three months after the induction of IL-13 expression (2 animals), and from ten wild-type (non-induced) controls. The analysis of lipids in tape strips collected from lesional areas of induced IL-13-TG animals recapitulated changes in lipid molecular species that was observed in human lesional AD stratum corneum samples (FIGS. 4A-4C). Notably, both sphingomyelins and NS-ceramides demonstrated a substantial increase in relative content of short-chain species (in particular, 16:0-species) with a decline in the relative content of long-chain species (especially in N-26:0-NS-CER and 26:0-SM) in the lesional skin tape strip samples of IL-13-TG mice, similar to what was observed in human AD lesional stratum corneum. Furthermore, lesional stratum corneum from IL-13-TG mice demonstrated changes in LPC molecular species involving an increase in short-chain species (18:0-LPC) and a decline in relative percentage of the long-chain LPC species (24:0- and 26:0-LPC). Thus, the mouse model of IL-13-driven AD development demonstrated almost identical to human AD changes in the profile of molecular species in several lipid classes.

Figure 5A:
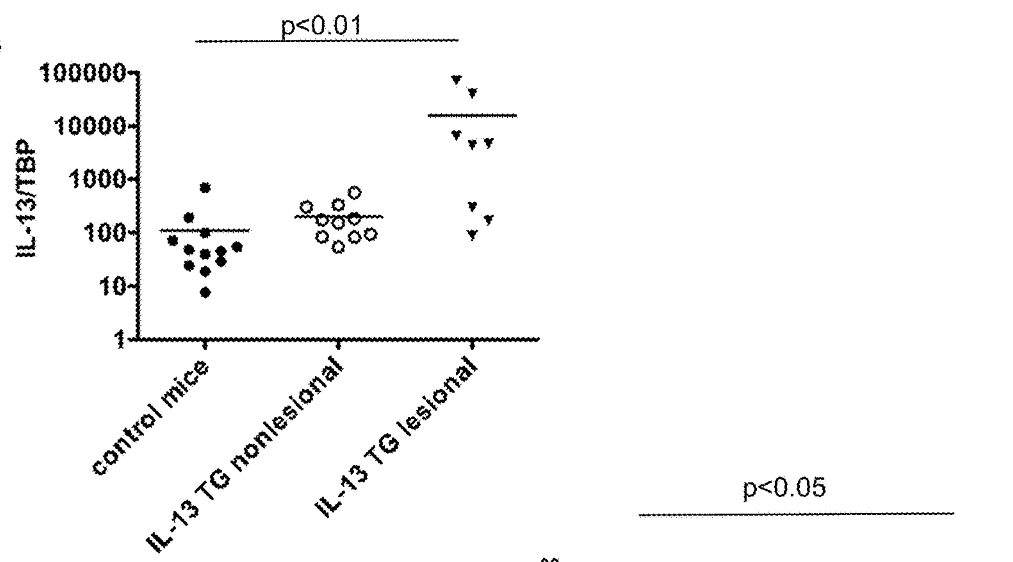
FIGS. 5A-5C show the expression of interleukin-13 (IL-13) (FIG. 5A), ELOVL3 (FIG. 5B) and ELOVL6 (FIG. 5C) in skin of IL-13-TG mice and control animals as detected by real time PCR. An increased expression of IL-13 mRNA and significant downregulation of ELOVL3 and ELOVL6 mRNA expression was observed in lesional skin of IL-13-TG mice. n=8-12 animals
Figure 5B:
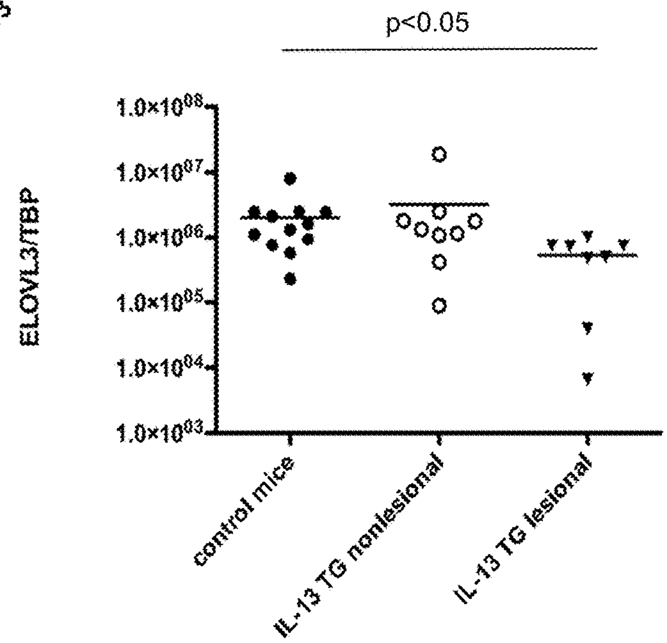
Figure 5C:
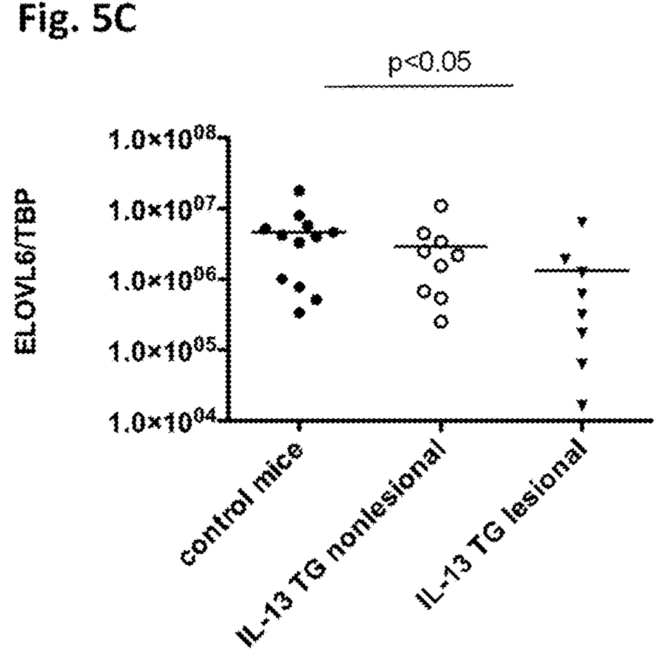

To confirm that the formation of skin lesions in K5-tTA-IL-13 transgenic mice is linked to IL-13 production, IL-13 was quantified by RT-PCR in skin biopsies obtained from lesional as well as non-lesional areas of the skin in the induced animals and from biopsies obtained from non-induced control animals. FIG. 5A demonstrates a significant induction of IL-13 level in lesional areas of mouse skin and its minimal level in non-lesional skin from induced animals and in the skin of control non-induced animals. RT-PCR analysis of mouse skin biopsies also revealed significant downregulation of ELOVL3 and ELOVL6 mRNA in the lesional skin of IL-13 transgenic mice (FIGS. 5B, 5C).

Example 4

This example shows that Th2 Cytokines and IL-17 have distinct effects on sphingolipid metabolism in differentiated primary human keratinocytes.

Methods: Lipid profiles were examined by targeted liquid chromatography tandem mass spectrometry in Ca2+ differentiated primary human keratinocytes in the presence or absence of IL-4/IL-13 or IL-17a. Cellular expression of selected enzymes of lipid metabolism was examined by real-time PCR.

Results: Keratinocyte differentiation resulted in significantly increased levels of long-chain C22-C28 ceramides. However, cells differentiated in the presence of IL-4/IL-13 had a significant decrease in total ceramide levels (Mean±SD 14,984±731 vs. 36,339±6751 pmol/nmol lipid phosphorus in differentiated keratinocytes, $p<0.05$) and a qualitative decrease in long-chain ceramides. In contrast to IL-4/IL-13, IL-17a significantly increased total ceramide production (107,289±2,599 pmol/nmol lipid phosphorus, $p<0.05$) and resulted in nonselective increase of all ceramide molecular species. IL-4/IL-13 significantly reduced expression of glucosylceramides in differentiated keratinocytes (1,748±36 vs. 2,825±369 pmol/nmol lipid phosphorus, $p<0.05$, IL-4/IL-13-treated vs non-treated cells, respectively). IL-4/IL-13 significantly increased expression of fatty acid elongases ELOVL1, ELOVL3 and ELOVL5, ceramide synthases CERS3, CERS4, and glucosylceramide synthase UGCG.

Conclusions:

Keratinocyte differentiation in the presence of IL-4/IL-13 in vitro recapitulates changes in ceramide levels and molecular species redistribution in AD skin. These changes are accompanied by altered expression of fatty acid elongases, ceramide synthases and glucosylceramide synthase.

These observations reinforce the role of IL-4/IL-13 in driving skin barrier dysfunction in AD.

Example 5

This example shows the effects of type 2 cytokines on sphingolipid metabolism in cultured primary human keratinocytes are STAT6-dependent.

Keratinocytes are the major cells in the skin that form the stratum corneum and its lipids. To model the effects of type 2 cytokines on keratinocyte lipid metabolism, primary human keratinocytes grown in a submerged culture were used, differentiated in the presence of 1.3 mM $CaCl_2$ and treated in the presence or absence of IL-4 and IL-13 during the entire differentiation period.

Upon differentiation, keratinocyte sphingolipids undergo substantial changes. Notably, the relative proportion of long-chain (N-24:0-28:0-) molecular species of ceramides preferentially increases over short-chain (N-14:0-22:0-) species (FIG. 6A) that corresponds to prevailing presence of long-chain ceramides in mature stratum corneum. When keratinocytes were treated with type 2 cytokines during differentiation, cytokine presence had complex effect on ceramides as well as other sphingolipids. In particular, IL-4/IL-13 treatment led to a substantial increase in ceramide and sphingomyelin content with some preferential increase in short chain species (sphingoid bases N-acylated with C16-C20 fatty acids). However, LPC levels and their relative composition in differentiated keratinocytes did not change significantly upon type 2 cytokine treatment.

Figure 6D:
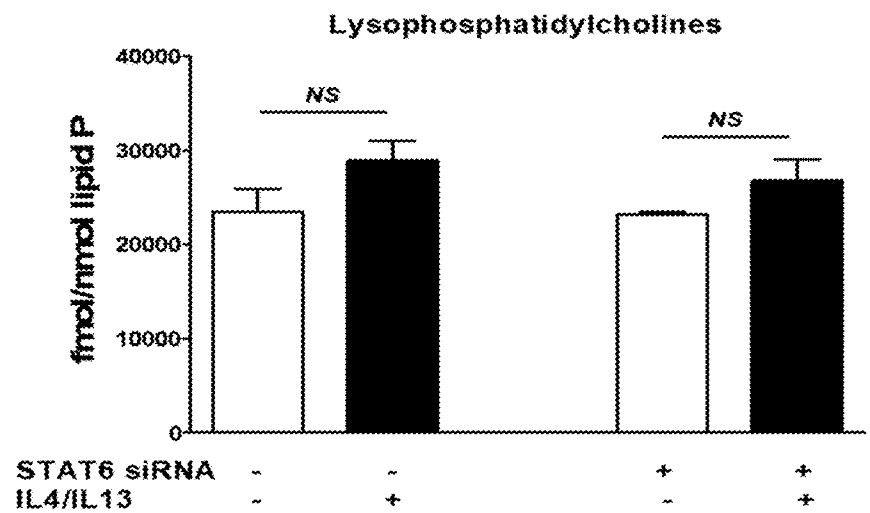
Figure 7A:
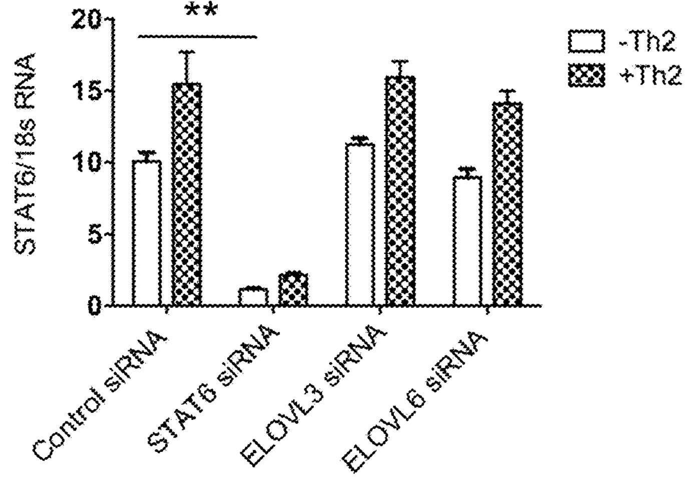
FIGS. 7A-7F show type 2 cytokines regulation of ELOVL3 and ELOVL6 expression in primary human keratinocytes. Keratinocytes were differentiated in the absence or presence of IL-4/IL-13. Keratinocytes were transfected with control siRNA, STAT6 siRNA ELOVL3 siRNA, ELOVL6 siRNA or ELOVL3/ELOVL6 siRNA and underwent Ca2+ differentiation for the period of time indicated. The expressions of STAT6 mRNA (FIG. 7A and FIG. 7D), ELOVL3 mRNA (FIG. 7B and FIG. 7E), ELOVL6 (FIG. 7C and FIG. 7D) were analyzed.
Figure 7B:
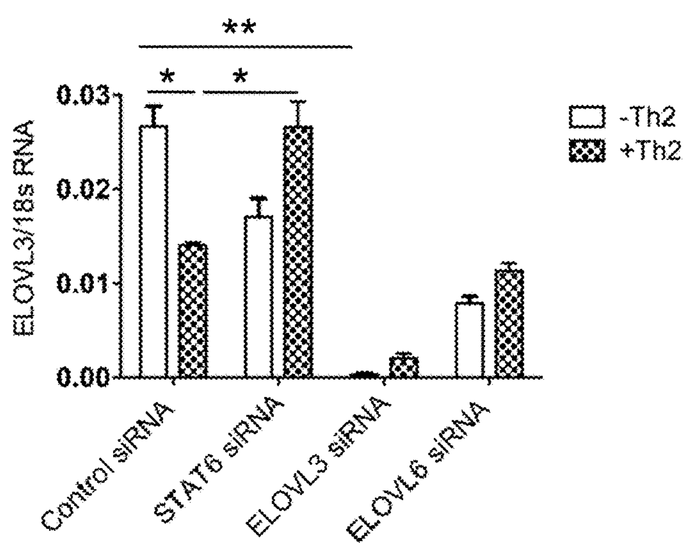
Figure 7C:
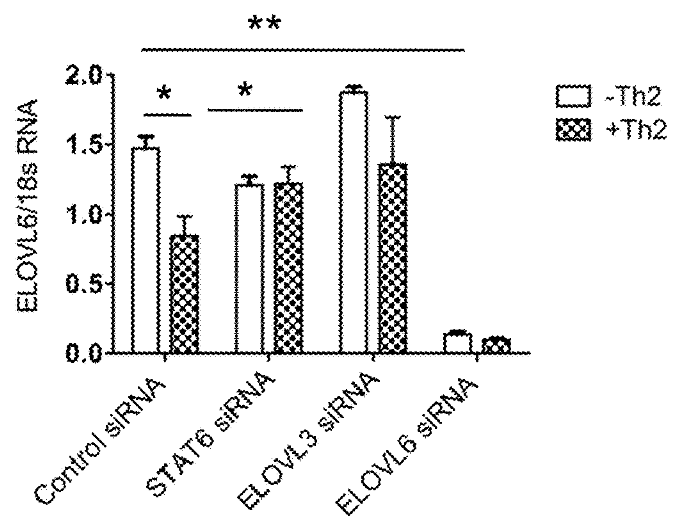
Figure 7D:
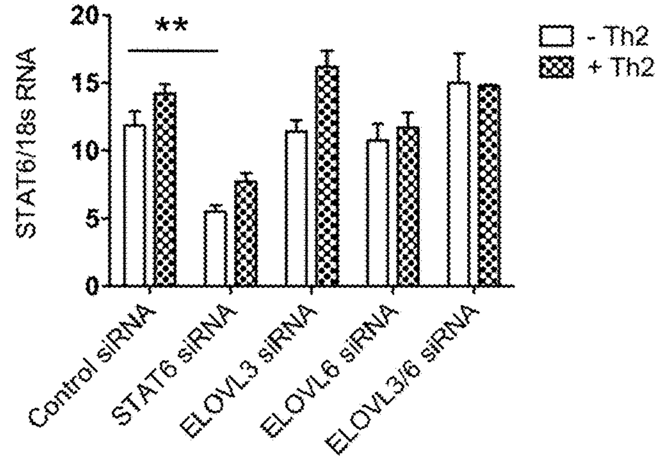
Figure 7E:
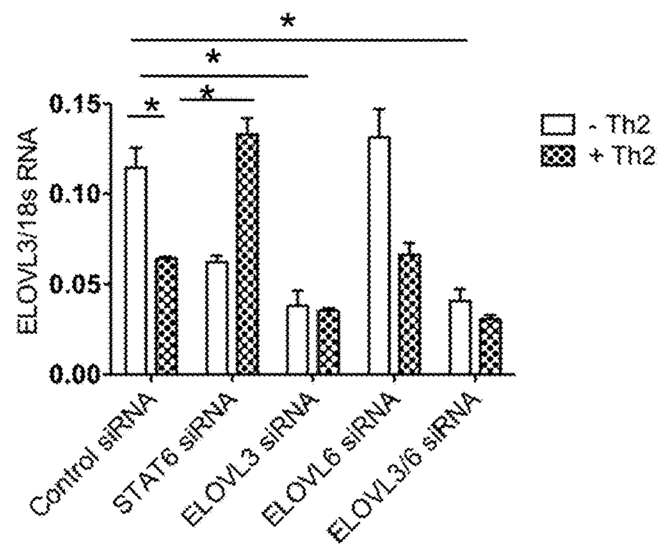

STAT6 is a master transcriptional regulator of IL-4/IL-13-induced signaling in cells. To test if STAT6 controls IL-4/IL-13-induced changes in sphingolipids, human keratinocytes were transfected with STAT6 siRNA or control nontargeting siRNA and differentiated keratinocytes cultures for five days in the presence of 1.3 mM $CaCl_2$. Some cells were also treated with IL-4/IL-13 during the entire differentiation period. As shown in FIGS. 6B and 6C, STAT6 silencing completely blocked the IL-4/IL-13-induced upregulation in ceramide and sphingomyelin levels. Neither IL-4/IL-13 treatment nor STAT6 silencing had affected the LPC content in cells (FIG. 6D). Significant inhibition of STAT6 mRNA expression by STAT6 siRNA in keratinocyte cultures was confirmed by RT-PCR (FIGS. 7A and 7D).

Figure 7F:
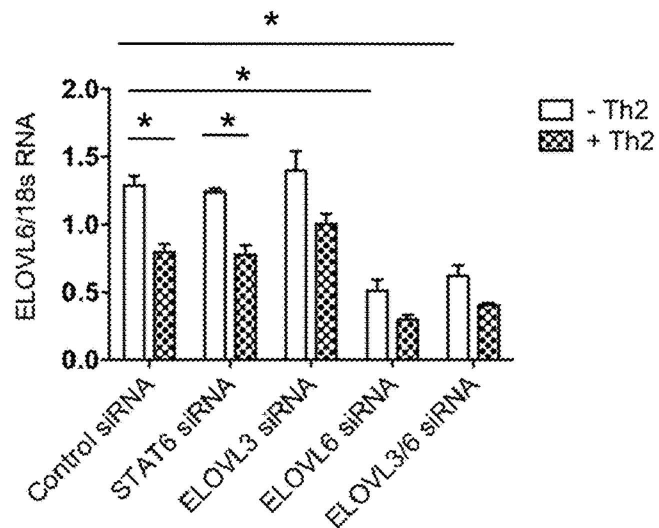

To test if Type 2 cytokines had an effect on the expression of elongases ELOVL3 and ELOVL6, human keratinocytes were treated with IL-4/IL-13 with simultaneous downregulation of STAT6, ELOVL3, or ELOVL6 expression by siRNA. IL-4/IL-13 treatment resulted in downregulation of ELOVL3/6 expression in differentiated keratinocytes (FIGS. 7B, 7C, 7E,7 F). Inhibition of STAT6 restored the expression levels of both ELOVL3 and ELOVL6 mRNA (FIGS. 7B, 7C,7 E). However, ELOVL6 mRNA expression was suppressed by IL-4/IL-13 in the presence of STAT6 siRNA at the later time point (FIG. 7F). Regulation of ELOVL3 expression by IL-4/IL-13 was confirmed by immunostaining, as decreased levels of ELOVL3 were observed in differentiated keratinocytes treated with IL-4/IL-13, while STAT6 inhibition restored ELOVL3 expression in IL-4/IL-13 treated keratinocytes. Very low ELOVL3 expression was observed in ELOVL3 siRNA transfected keratinocytes. No effects of ELOVL6 siRNA on the expression of ELOVL3 in keratinocytes was found. Thus, this data demonstrate the interrelationship between the expression of STAT6 and elongases ELOVL3 and ELOVL6.

Simultaneously, downregulation of ELOVL3 and ELOVL6 expression with siRNA upregulated short-chain fatty acids globally as shown by the analysis of total fatty acids in all glycerolipids, increased relative proportion of LPC with palmitic acid, and decreased relative levels of long-chain species in NS-ceramides and sphingomyelins (FIGS. 10A-10D).

Example 6

This example provides the methods used in the above examples.

Study Subjects.

Skin samples were obtained from 30 adult Caucasian subjects with active AD and 25 nonatopic healthy individuals with no personal and family history of atopy and skin diseases. AD patients were characterized by Investigator's Global Assessment (IGA) score, eczema area and severity index (EASI) and information about the body surface area covered by lesions. Patients had not received topical corticosteroids, topical calcineurin inhibitors, topical or oral antibiotics for one week prior to enrollment. Patients were not treated with systemic immunosuppressive medications for more than one month prior to enrollment into this study. The study was approved by the Institutional Review Board at National Jewish Health, Denver, Colo. All subjects gave written informed consent prior to participation in the study. A summary of study subjects' characteristics is provided in Table 3.

TABLE 3

Study subjects characteristics.

| | AD n = 30 | Healthy controls n = 25 |
|---|---|---|
| Age, years (Mean ± SE) | 38.4 ± 2.4 | 34.8 ± 2.1 |
| Gender (Male/Female) | 20/10 | 9/16 |
| Total serum IgE, kU/L (Mean ± SE) | 3184 ± 1806 | ND |
| EASI (Mean ± SE) | 22.7 ± 4.4 | NA |
| IGA | | |
| 2 = mild | 5 | NA |
| 3 = moderate | 19 | |
| 4 = severe | 6 | |
| Body surface area covered by lesions, % | 37 ± 4 | NA |
| Positive skin culture for *Staphylococcus aureus* | 12 out of 30 | 2 out 25 |

ND—not done,
NA—not applicable

Skin Swab Bacterial Cultures.

Skin swabs were collected from lesional and non-lesional skin of AD patients and from skin of healthy control subjects. Blood agar plates were inoculated and cultured for 24 hours. Slide coagulase and catalase tests were performed for the identification of *Staphylococcus aureus* isolates.

Serum IgE Assessment.

Measurements of total serum IgE for atopic dermatitis patients were performed using standard immunological procedures as refered in Matricardi P M et al. EAACI Molecular Allergology User's Guide. Pediatr Allergy Immunol. 2016 May 27 Suppl 23:1-250.

Skin Tape Strip Collection.

A total of 20 consecutive D-SQUAME® tape strips (22 mm diameter, CuDerm, Dallas, Tex.) were collected from the volar surface of the forearm. Non-lesional skin from AD patients and skin from healthy control subjects were sampled. In addition, tape strip samples from lesional skin were collected from 15 AD patients in the study group. On application of the first tape disc, 4 marks were placed around the disc with a marker so that subsequent discs could be applied to the same location. Each tape disc was placed adhesive side up in a separate well of the two 12-well plates allocated for sample collection. Plates were kept on dry ice during the tape strip collection. Tape strips #5 and #6 were designated for lipid analysis and stored at −80° C. until lipids were extracted. Tape strips #11 through #20 were allocated for RNA extraction.

Tape Strip Processing for Lipid Extraction and Protein Estimation.

Stratum corneum from tape strips #5 and #6 (human subjects) or tape strips ##1-12 (mice) was removed by scraping tape strips in 2 ml water-methanol (9:1, v/v) mixture in a Petri dish with a rubber cell scraper. Floating stratum corneum particles were carefully transferred into 8 ml glass screw cap tubes then subjected to a modified Bligh and Dyer extraction (Bligh E G, and Dyer W J. A rapid method of total lipid extraction and purification. *Can J Biochem Physiol.* 1959; 37(8): 911-7). A mixture of lipid internal standards was added during initial step of lipid extraction to ensure absolute quantitation of targeted lipid subclasses. In brief, extraction was performed overnight by adding additionally 0.5 ml methanol and 1 ml chloroform, then phase separation was achieved by adding 1.5 ml chloroform and 1.35 ml 2% formic acid, intensive vortexing and centrifugation (2,000 g×10 min). After centrifugation, the upper water-methanol phase was carefully removed, then bottom chloroform phase was collected with minimal disturbance to a protein interphase, evaporated by a stream of nitrogen, and lipids were dissolved in 0.2 ml methanol for LC-ESI-MS/MS analyses. The residual protein denaturates/pellets were dried out by a stream of nitrogen, then hydrolyzed with 1 ml of 2N sodium hydroxide overnight at 37° C. on a shaking water bath essentially as described in (Dreher F, et al. Colorimetric method for quantifying human Stratum corneum removed by adhesive-tape stripping. Acta Derm Venereol. 1998; 78(3):186-9) with slight modifications. Tubes were periodically vortexed and sonicated on a sonicating water bath during first hours of hydrolysis. After 16-24 h of hydrolysis, sodium hydroxide was neutralized with 1 ml 2N hydrochloric acid, hydrolyzed proteins were centrifuged at 2000 g for 5 min and protein concentrations were determined using DC protein assay kit (Bio-Rad, Hercules, Calif.) with bovine serum albumin (BSA) as a protein standard. It was initially determined that BSA is not needed to be hydrolyzed for determination by DC protein assay as both non-hydrolyzed and hydrolyzed BSA provide the same readings.

Lipid Analysis by Targeted Lipid Chromatography Tandem Mass Spectrometry.

Ceramides, LPC and SM were identified and quantified using targeted liquid chromatography electrospray ionization tandem mass spectrometry (LC-ESI-MS/MS) approach on Sciex 6500QTRAP mass spectrometer coupled with Shimadzu Nexera X2 UHPLC system. All molecules were detected in positive ions mode. SM and LPC were detected as a transition from corresponding molecular ions to the m/z 184 (indicative of a phosphocholine group). All ceramides were detected as a transition from molecular ions to the most characteristic product ions. C18-NS- and C18-AS-Ceramides (ceramides with C18-sphingosine as a sphingoid base) were detected as a transition to the m/z 264. Similarly, C20- and C22-NS-ceramides were detected as a transition to the m/z 292 and m/z 320, correspondingly. C18-NDS-ceramides were detected as a transition to the m/z 266. C18-NP- and C18-AP-ceramides were detected as a transition to the m/z 300. EOS-ceramides were detected as a transition to the m/z 264, m/z 292, and m/z 320 as our preliminary work have identified all three sphingoid bases being present in EOS ceramides. Global glycerolipid fatty acids were determined as fatty acid methylamides after sample hydrolysis with methylamine reagent (Clarke N G, and Dawson R M. Alkaline O leads to N-transacylation. A new method for the quantitative deacylation of phospholipids. *Biochem J.* 1981; 195(1):301-6). Fatty acids were determined in positive ions as a transition from corresponding fatty acid methylamide molecular ions to the m/z 32 and expressed as a relative percentage of the sum of the ions. Chromatography was performed on Ascentis Express RP-Amide 2.7 μm 2.1×50 mm column using gradient elution from methanol:water:formic acid (65:35:0.5, 5 mM ammonium formate) to methanol:chloroform:water:formic acid (90:10:0.5:0.5, 5 mM ammonium formate). D7-16:0-Ceramide (N-16:0-D7-sphingosine), 13:0-LPC, and N-12:0-sphingosylphosphorylcholine (12:0-SM) were used as the internal standards. Standard curves of variable amounts of analites versus fixed amount of internal standard were created for 14:0, 16:0-, 18:0-, 20:0-, 22:0-, 24:1- and 24:0-analogs of ceramides, dihydroceramides, sphingomyelins, and lysophosphatidylcholines using available standards from Avanti Polar Lipids (Alabaster, Ala.). Relative amounts of EOS ceramides were determined in a semi-quantitative way by using a correction factor from 24:0-NS-ceramide standard curve.

RNA Preparation from Skin Tape Strips.

Collected tape strips #11 through #20 from human skin were sequentially scraped into the RLT buffer (Qiagen) on the day of collection and frozen at −80° C. RNeasy Micro Kits (Qiagen) were used according to the manufacturer's protocol to isolate RNA from skin tape strips.

RNA Transcriptome Gene Expression and Quality Control.

RNA Ampliseq libraries were constructed and barcoded with the ION AMPLISEQ™ Trasncriptome Human Gene Expression Kit and methods. Barcoded RNA-seq libraries were pooled and sequenced on the Ion Torrent Proton sequencer using P1 chips.

Sequencing reads were mapped to Ampliseq transcriptome target regions with the torrent mapping alignment program (TMAP) and quantified with the Ion Torrent ampliSeqRNA plug-in, using the uniquely mapping option. Duplicated sequences were removed from the FASTA file and incorrect amplicon locations were corrected (Reynolds S D, et al. Airway Progenitor Clone Formation Is Enhanced by Y-27632-Dependent Changes in the Transcriptome. *Am J Re spir Cell Mol Biol.* 2016; 55(3):323-36). To combat potential bias from sequencing depth, the counts of each sample were downsampled to $8\times10^6$ reads. The gene counts were normalized and differential expression performed using the DESeq2 R package (Love M I, et al. Moderated estimation of fold change and dispersion for RNA-seq data with DESeq2. *Genome Biol.* 2014; 15(12):550) (distributed via Bioconductor (Huber W, et al. Orchestrating high-throughput genomic analysis with Bioconductor. *Nat Methods.* 2015; 12(2):115-21)). Multiple testing correction was performed by applying Benjamini-Hochberg false discovery rate (FDR) of 0.05 for significance.

IL-13 Transgenic Mice.

Skin-specific inducible K5-tTA-IL-13 transgenic mice were generated as described (Zheng, T, et al. 2009). The genotypes of the mice were determined by PCR using specific primers for K5-tTA, and TRE-Tight-IL-13 (Zheng, T, et al. 2009). Doxicyclin (DOX) was added to the drinking water (1 mg/ml) to suppress tTA and to keep the IL-13 transgene off until K5-tTA-IL-13 mice were 6 weeks old. The experiments were initiated by withdrawing DOX from the drinking water. In all experiments, TG(−) littermate controls received the same amount of DOX or no DOX for the same length of time. TG(+) and TG(−) mice were examined for skin lesions and clinical scores for disease severity were recorded. After mice were euthanized by carbon dioxide inhalation, lesional and non-lesional skin was excised using a 4 mm biopsy punch (Miltex Inc., York, Pa.) and preserved in TRI reagent (Sigma-Aldrich, St. Louis, Mo.) for RNA extraction. Separately, twenty skin tape strips (D-SQUAME® tape strips, 10 mm diameter, CuDerm, Dallas, Tex.) were collected from lesional and non-lesional sites of TG(+) mice and from normal skin of the TG(−) littermates. Prior to tape strip collection, animals were shaved and the remaining fur was removed using NAIR™.

Primary Human Keratinocyte Cell Culture.

Keratinocyte cultures were grown in EpiLife cell culture medium (Life Technologies, Grand Island, N.Y.) with human keratinocyte growth supplement S7 (Life Technologies), 0.06 mM $CaCl_2$, and gentamicin/amphotericin. Keratinocytes were treated with IL-4/IL-13 (R&D Systems, Minneapolis, Minn.), or media for 24 hours (undifferentiated) or differentiated with media containing 1.3 mM $CaCl_2$ for up to 5 days with or without cytokines. Lipid extracts were prepared for analysis as skin tape strips above.

Quantitative Real Time PCR (RT-PCR).

Murine biopsies were preserved in TRI reagent (Sigma-Aldrich). Total RNA was isolated from murine skin biopsies according to manufacturer's guidelines (Sigma-Aldrich), followed by clean up using Qiagen RNeasy Mini Kit (Qiagen, Valencia, Calif.). Qiagen RNeasy Mini Kit was used for the RNA extraction from keratinocyte cultures. RNA was reverse-transcribed into cDNA using the SUPERSCRIPT® VILO™ MasterMix (Life Technologies). RT-PCR was performed and analyzed by the dual-labeled fluorogenic probe method using ABI Prism 7300 real time PCR machine (Applied Biosystems, Foster City, Calif.). Primers and probes for 18s RNA, murine TAT box binding protein (TBP), murine IL-13, murine ELOVL1-7, human ELOVL3, ELOVL6, STAT6 were purchased from Applied Biosystems. Amplification reactions were performed in MicroAmp optical plates (Applied Biosystems) in a 25-μL volume as previously described (Howell M D, et al. Cytokine modulation of atopic dermatitis filaggrin skin expression. *J Allergy Clin Immunol.* 2007; 120(1):150-5). Data was normalized to 18s RNA levels or TBP levels as endogenous controls.

siRNA Transfection.

Primary human keratinocytes were transfected according to the manufacturer's instructions using Lipofectamine 2000 (Invitrogen) with 20 nM control nontargeting siRNA, STAT6 Smartpool siRNA, ELOVL3 Smartpool siRNA, ELOVL6 Smartpool siRNA (Dharmacon, Lafayette, Colo.) in antibiotic free media, followed by treatment with IL-4/IL-13 and differentiation for up to 5 days in 1.3 mM $CaCl_2$ supplemented EpiLife as above. Cells were scraped off in methanol then lipid extracts were prepared for analysis as skin tape strips above.

Cell Staining and Microscopy.

Immunofluorescence staining was performed using keratinocytes grown on cover slips. Cells were fixed with 4% paraformaldehyde and permeabilized briefly with PBS/0.01% saponin/0.05% Triton X-100. After blocking with SuperBlock (SkyTec, Logan, Utah), cells were incubated with anti-ELOVL3 antibody (Abcam, Cambridge, Mass.) overnight at 4° C., washed three times with PBS/0.05% triton X-100, followed by incubation with FITC conjugated donkey ant-rabbit F(ab)2 antibody (Jackson ImmunoLaboratories) and DAPI cell nuclei stain (Sigma, St. Louis, Mo.) for 1 h at room temperature. Images were taken with a Leica Microscope at 250× magnification using SlideBook 6.0 software (Intelligent Imaging Innovations, Denver, Colo.).

Statistical Analysis.

The Student t-test was used to determine the significance of difference between two groups, and one-way ANOVA was used for comparison among multiple groups. All data were expressed as mean±SEM. Difference with $p<0.05$ was considered statistically significant.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A method of diagnosing and treating an allergic disease in an asymptomatic subject, comprising:

a. obtaining at least one stratum corneum non-lesional skin sample from an asymptomatic subject, wherein the at least one skin sample is obtained by a skin tape stripping method;

b. determining the levels and/or relative percentages of lysophosphatidylcholine 24:0-LPC and short chain molecular species of at least one lipid selected from the group consisting of sphingomyelin 18:0-SM, and lysophosphatidylcholines 14:0-LPC, 16:0-LPC, and 18:0-LPC in the at least one skin sample obtained by a skin tape stripping method and normalizing the levels and/or relative percentages to total protein content in the same at least one skin sample;

c. comparing the normalized levels and/or relative percentages of the short chain molecular species of the at least one lipid in the at least one skin sample obtained by a skin tape stripping method to the same short chain molecular species of the at least one lipid from a healthy control sample obtained by a skin tape stripping method;

d. comparing the normalized levels and/or relative percentages of lysophosphatidylcholine 24:0-LPC in the at least one skin sample to lysophosphatidylcholine 24:0-LPC from a healthy control sample;

e. identifying the subject as having an allergic disease selected from atopic dermatitis and eczema when:

i. the normalized levels and/or relative percentages of short chain molecular species of the at least one lipid from the at least one skin sample are elevated as compared to the normalized levels and/or relative percentages of the same short chain molecular species of the at least one lipid from the healthy control sample; and ii. the normalized levels and/or relative percentages of lysophosphatidylcholine 24:0-LPC from the at least one skin sample are decreased as compared to the normalized levels and/or relative percentages of lysophosphatidylcholine 24:0-LPC from the healthy control sample; and f. administering an effective amount of a therapeutic to the subject identified as having an allergic disease selected from atopic dermatitis and eczema prior to development of symptoms, wherein the administration of the therapeutic delays the onset of symptoms of the allergic disease in the subject and/or reduces the severity of the allergic disease symptoms in the subject.

2. The method of claim 1, wherein the allergic disease is atopic dermatitis.

3. The method of claim 1, wherein the step of determining the levels and/or relative percentages of lysophosphatidylcholine 24:0-LPC and the short chain molecular species of the at least one lipid is by a method comprising mass-spectrometry.

4. The method of claim 1, further comprising determining the expression level of each of elongation of long chain fatty acids family member 1 (ELOVL1), elongation of long chain fatty acids family member 3 (ELOVL3), elongation of long chain fatty acids family member 4 (ELOVL4), and elongation of long chain fatty acids family member 6 (ELOVL6) in the at least one skin sample and in the healthy control sample.

5. The method of claim 1, wherein the therapeutic is selected from the group consisting of a moisturizer, an anti-inflammatory, a modifier of an enzyme of lipid metabolism, a long chain fatty acid derivative and combinations thereof.

6. The method of claim 1, wherein the method further comprises administration of a different therapeutic as compared to the therapeutic administered in step f.

* * * * *